United States Patent
Oraevsky et al.

(10) Patent No.: US 7,999,161 B2
(45) Date of Patent: Aug. 16, 2011

(54) LASER-ACTIVATED NANOTHERMOLYSIS OF CELLS

(76) Inventors: Alexander Oraevsky, Houston, TX (US); Dmitri Lapotko, Minsk (BY)

( * ) Notice: Subject to any disclaimer, the term of this patent is extended or adjusted under 35 U.S.C. 154(b) by 704 days.

(21) Appl. No.: 11/795,857

(22) PCT Filed: Jan. 22, 2006

(86) PCT No.: PCT/US2006/002186
§ 371 (c)(1),
(2), (4) Date: Jul. 23, 2007

(87) PCT Pub. No.: WO2006/078987
PCT Pub. Date: Jul. 27, 2006

(65) Prior Publication Data
US 2008/0160090 A1    Jul. 3, 2008

Related U.S. Application Data

(60) Provisional application No. 60/646,018, filed on Jan. 22, 2005.

(51) Int. Cl.
*C07K 16/00* (2006.01)
(52) U.S. Cl. ............ 977/700; 977/702; 530/387.1; 530/387.7; 424/93.1; 424/93.7; D24/158

(58) Field of Classification Search .............. None
See application file for complete search history.

(56) References Cited

OTHER PUBLICATIONS

Lapotko et al. (Lasers in Surgery and Medicine Jan. 20, 2005, 36(1): 22-30).*

* cited by examiner

*Primary Examiner* — Peter J Reddig
(74) *Attorney, Agent, or Firm* — Benjamin Aaron Adler

(57) ABSTRACT

Provided herein are methods and system to increase selective thermomechanical damage to a biological body, such as a cancer cell or cell associated with a pathophysiological condition. The biological body or cancer cell is specifically targeted with nanoparticulates comprising one or more targeting moieties which form nanoparticulate clusters thereon or therewithin. Pulsed electromagnetic radiation, e.g., optical radiation, having a wavelength spectrum selected for a peak wavelength near to or matching a peak absorption wavelength of the nanoparticulates selectively heats the nanoparticulates thereby generating vapor microbubbles around the clusters causing damage to the targets without affecting any surrounding medium or normal cells or tissues. Also provided is a method of treating leukemia using the methods and system described herein.

17 Claims, 14 Drawing Sheets

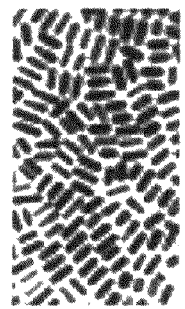 
Fig. 2A          Fig. 2B
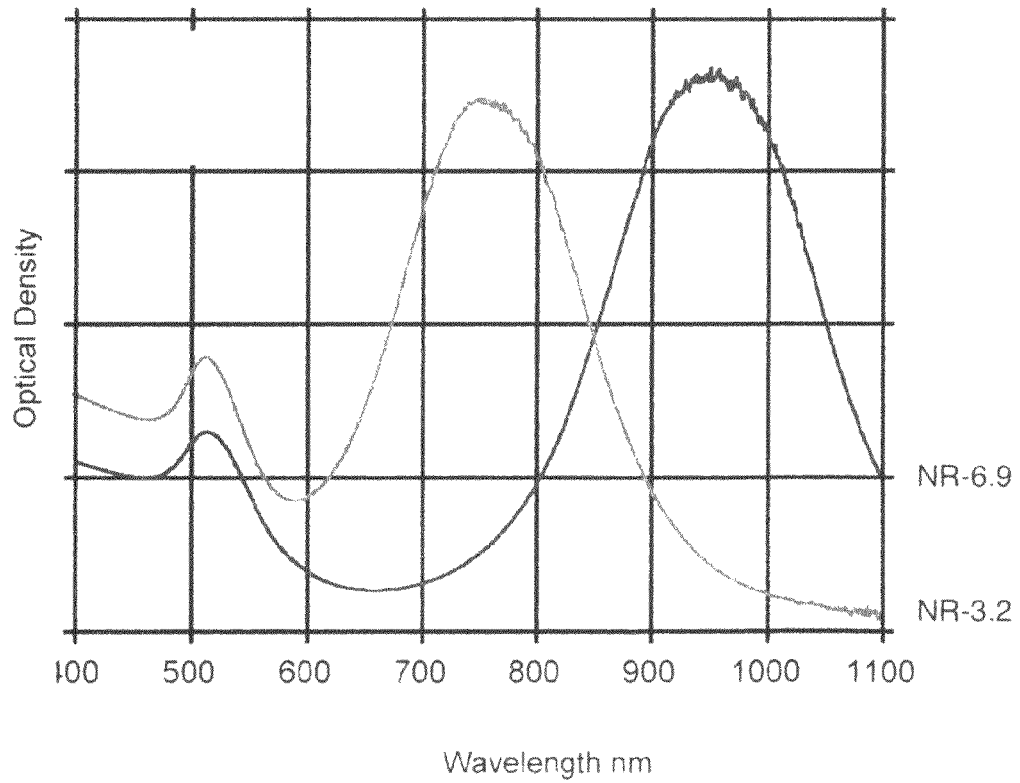
Fig. 2C

K-562 cells

Control
(undamaged whole cells)

Irradiated
(damaged cell fragments)

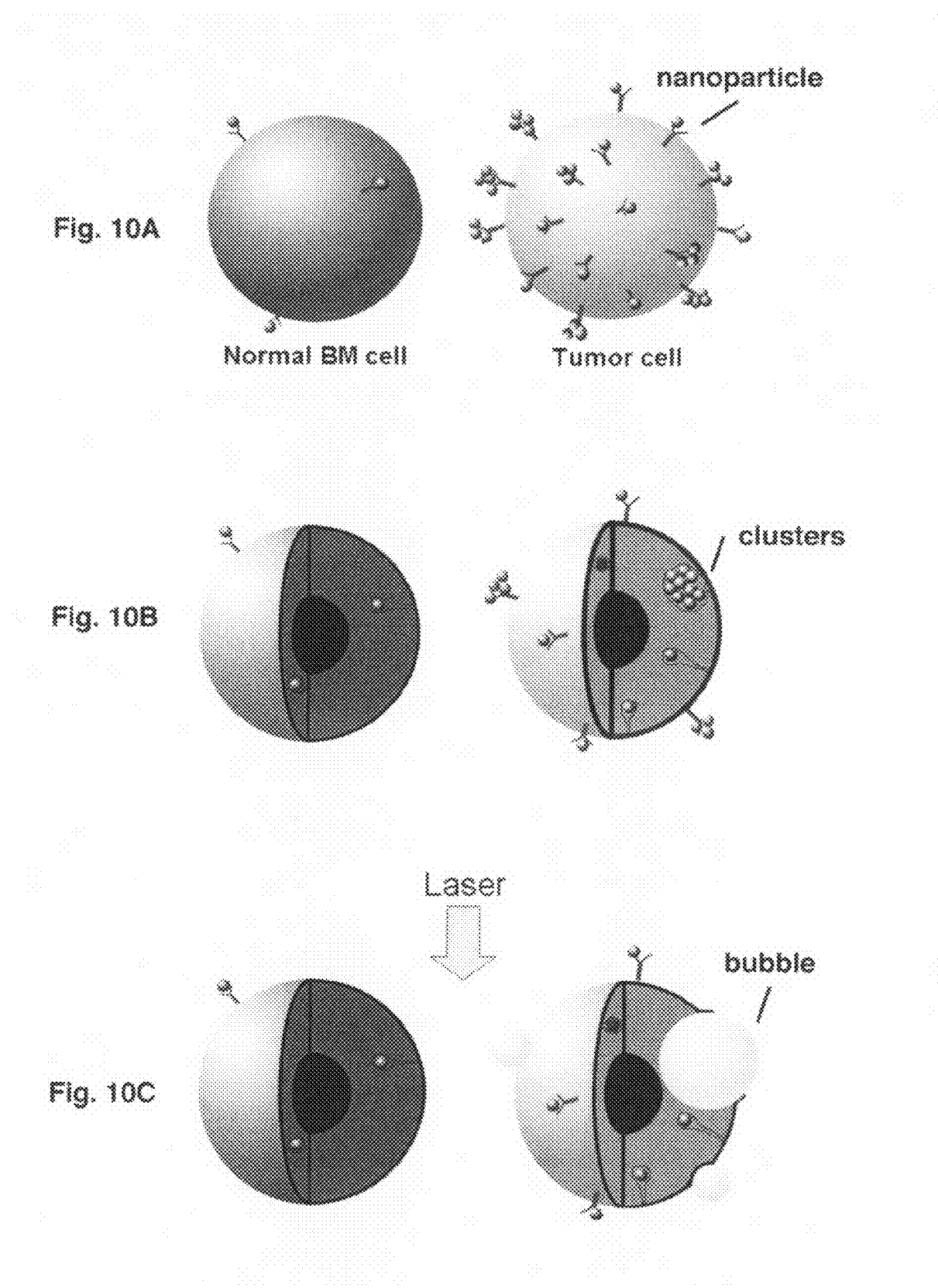

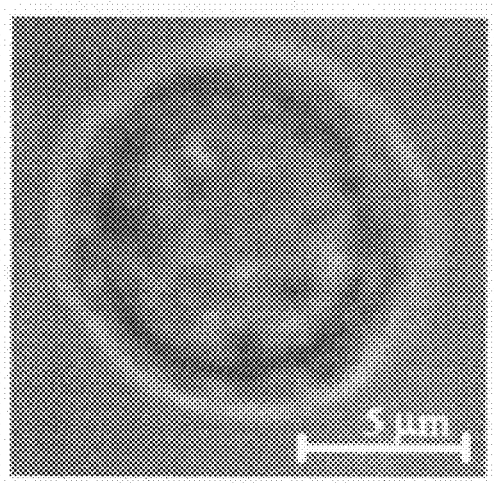
Fig. 11A
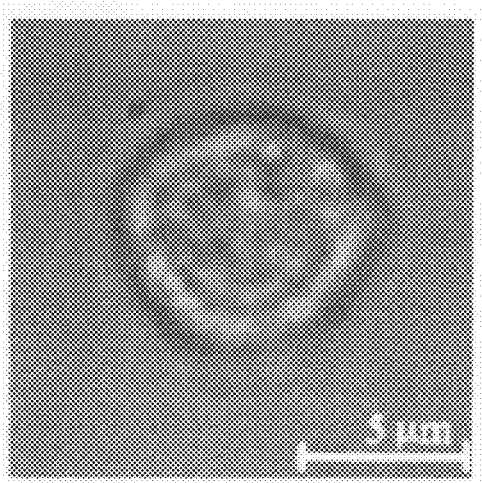
Fig. 11B
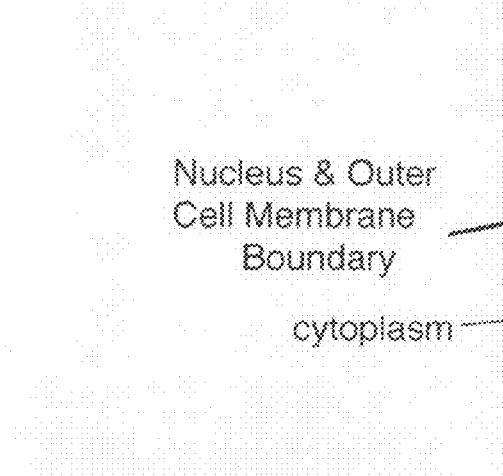
Nucleus & Outer Cell Membrane Boundary
cytoplasm
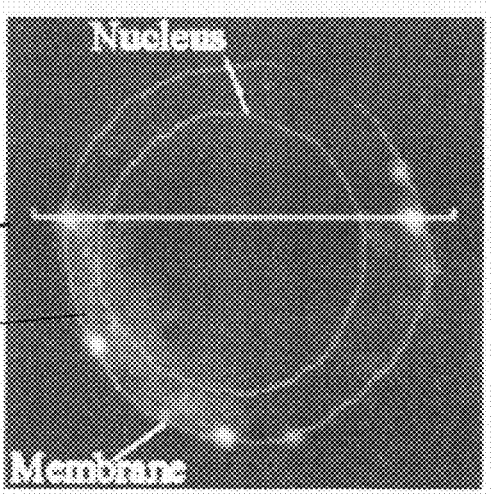
Fig. 11C
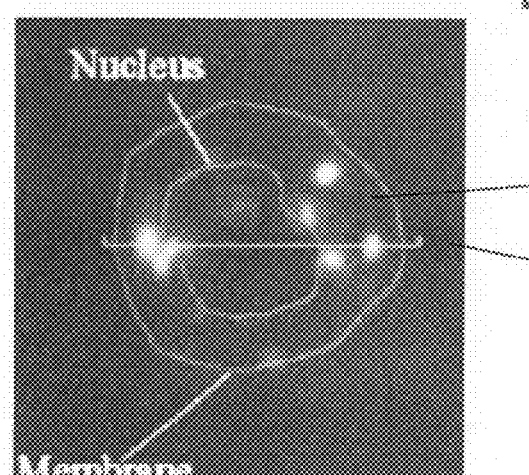
cytoplasm
Nucleus & Outer Cell Membrane Boundary
Fig. 11D peaks associated with cell membrane peaks associated with cell cytoplasm

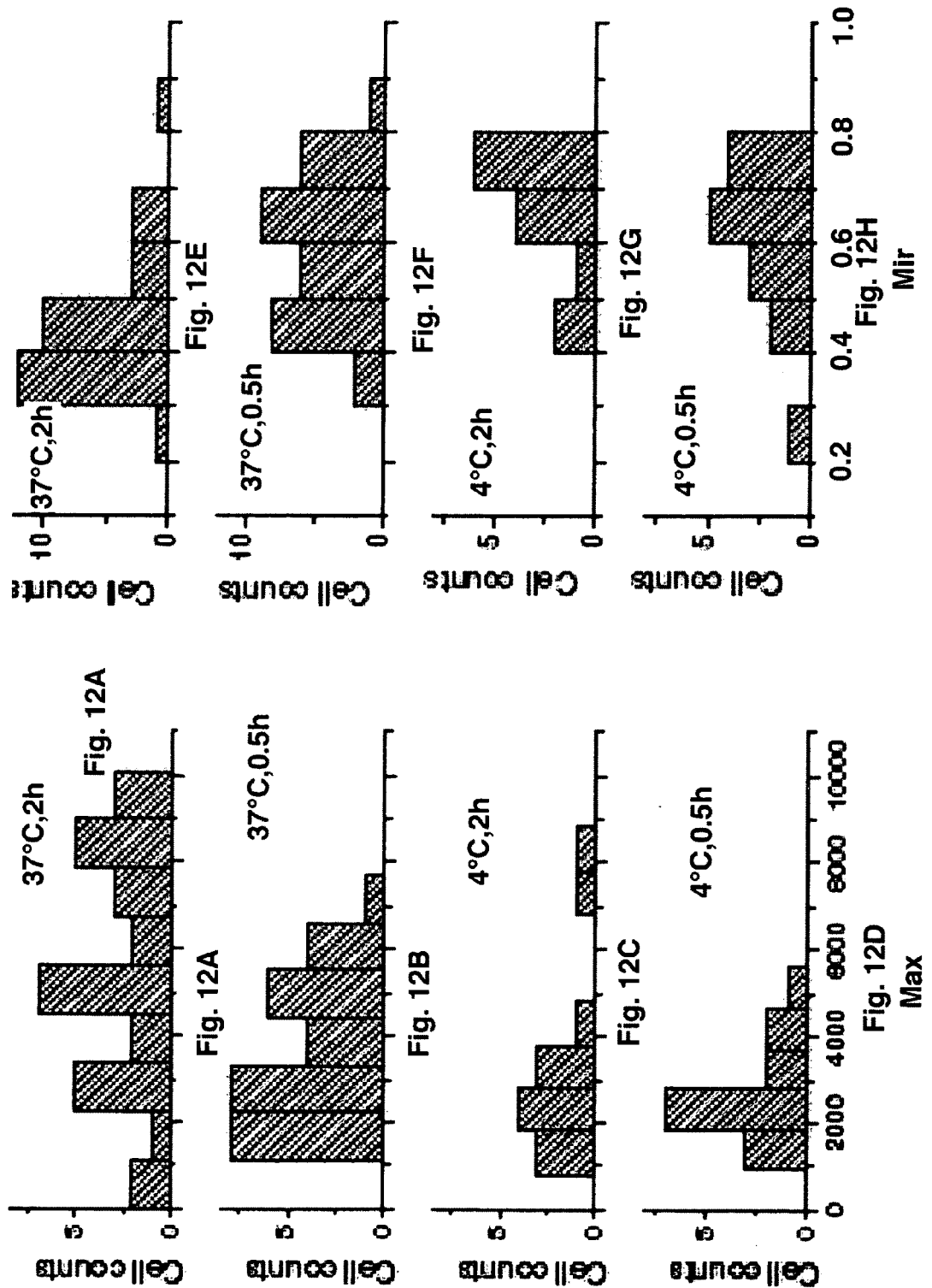

LASER-ACTIVATED NANOTHERMOLYSIS OF CELLS

CROSS-REFERENCE TO RELATED APPLICATION

This is a national stage application under 35 U.S.C. §371 of international application PCT/US2006/002186, filed Jan. 23, 2006, now abandoned, which claims benefit of priority under 35 U.S.C. §119(e) of provisional application U.S. Ser. No. 60/646,018, filed Jan. 22, 2005, now abandoned.

BACKGROUND OF THE INVENTION

1. Field of the Invention

The present invention relates to the fields of medical therapies employing electromagnetic radiation and of nanoparticles. More specifically, the present invention relates to a method and a system for electromagnetic radiation induced selective destruction of abnormal biological bodies or structures utilizing bioconjugated nanoparticles.

2. Description of the Related Art

In a variety of medical applications, it is desirable to inactivate, ablate or otherwise achieve the destruction and elimination of abnormal cells, while preserving normal and healthy cells. Examples of abnormal cells include, but are not limited, to cancer (tumor) cells, microorganisms (bacteria) harmful to humans and atherosclerotic plaques. Recent advances in biomedical optics and nanotechnology has created a solid basis for development of effective therapies for human diseases, such as cancer or atherosclerosis. The major breakthrough in this area is the possibility for a therapeutic agent to target selectively certain types of cells with molecular specificity. Furthermore, new imaging modalities are being developed to visualize not only abnormal cells and tissues, but also to monitor and guide therapeutic procedures, making them more effective and safe. The prior art discloses laser (optical) methods of therapy, which can be, in principle, guided by imaging based on optical contrast or otherwise enabled by optical activation.

Selective and specific inactivation, that is, damage or destruction, of cells with optical means requires substantial optical contrast between target cells and all non-target normal cells. General approaches to achieve cell inactivation include thermomechanical damage through high-intensity pulsed laser interaction with cells, thermal damage through continuous wave high power interaction, such as used for hyperthermia and coagulation, and biochemical damage through relatively low power interactions of photons with molecules resulting in production of chemically active species, such as ions, radicals and metastable excited states (1). Similarly, these types of interactions can be the result of interactions of electromagnetic radiation of various wavelengths, e.g., X-rays, UV, visible light, near-infrared, infrared photons, microwave, and radiofrequency quanta, and also high intensity acoustic waves. Other types of radiation are very expensive to produce and, therefore, not practical.

Laser ablation is based on thermal and mechanical effects caused in cells by absorption of high-intensity laser pulses (2). One of the advanced concepts of laser ablation, selective photothermolysis, was introduced more than 20 years ago (3). Selective photothermolysis employs short laser pulsed interaction with absorbing tissue microstructures to induce localized physical damage by avoiding thermal diffusion of the deposited laser energy. Other advanced concepts of precise laser ablation with limited thermal collateral damage to surrounding tissue employs conditions of pressure confinement upon short pulse laser irradiation to produce tensile wave causing cavitation bubbles at temperatures below 100° C. (4) or ultrashort laser pulses to cause nonlinear absorption and rapid micro-explosion that occurs prior to thermal diffusion (5). Slow heating with long pulses of electromagnetic radiation can also be used for selective damage of cells, however, due to thermal diffusion requires much stronger optical contrast to achieve specificity and to not damage adjacent cells or tissues (6). As an alternative to instantaneous thermomechanical destruction of target cells, photodynamic therapy employs low-intensity laser irradiation to produce necrosis and apoptosis through delayed damage mechanisms caused by photochemically produced toxic species, for example, radicals and singlet oxygen (7).

Both high and low intensity interactions of laser radiation with cells can be made selective and specific to target cells. Such selectivity requires utilization of either endogenous or exogenous chromophores, which strongly absorb specific colors of laser spectrum in the visible and near-infrared, i.e. in the range of wavelengths where majority of tissue constituents do not absorb. Since endogenous tissue chromophores strongly absorbing in the red and near-infrared are limited to hemoglobin and melanin, the medical applications of natural contrast agents are limited to blood vessels and retinal pigmented epithelium (8,9). Selective damage of leukemia and other cancerous cells demands exogenous contrast agents. Optical contrast agents that possess very strong absorption of near-infrared radiation attract attention of researchers because normal cells and tissues are transparent in this spectral range, so there is a great potential to achieve an exceptional selectivity of cell damage through the contrast agent. Chromophore-assisted laser inactivation (CALI) is a term to describe selective inactivation of certain proteins in cellular membranes using laser irradiation of cells stained with molecular dyes strongly absorbing red laser pulses (10).

It was recently revealed that gold nanoparticles can be designed to absorb any desirable color of near-infrared radiation by either changing the thickness gold shells on the silica core (11) or changing the aspect ratio of gold nanorods, i.e., ellipsoids or other prisms with one elongated axis (12). Gold nanoparticles and especially silver nanoparticles absorb near-infrared light much stronger than nanoparticles of organic dyes, which makes them superior contrast agents for imaging a small cluster of cancer cells in the depth of tissue (13). Nanoparticle assisted selective laser thermolysis of cells was recently demonstrated by targeting optically absorbing nanoparticles to cell surface receptors and superheating them with laser pulses (14). Based on the experimental results obtained with microparticles, the prior art speculated that the cavitation bubble generation that results in cell inactivation after laser irradiation with certain optical fluence may depend on particle size. On the other hand, the prior art neither provides an explanation of the underlying physical phenomena, nor provides a solution for achieving highly effective cell damage using low threshold fluence of electromagnetic radiation.

U.S. Pat. No. 6,530,944 teaches optically active nanoparticles that can be used in therapeutic and diagnostic methods. However, therapeutic applications disclosed by West et al. are limited to methods of hyperthermia, i.e. slow heating usually with continuous wave lasers and other optical sources. Nanoparticles will extravasate preferentially at locations where the blood vessel walls have increased porosity or have microvascular surface changes, especially at tumor sites. O'Neal et al. demonstrated that intravenous injection of gold nanoshells, which are nanoparticles strongly absorbing in the near-infrared spectral range, into a mouse, resulted in nonspecific, but effective targeting of an implanted tumor. Further, it enabled hyperthermic damage of the tumor through heating the nanoshells to temperatures several degrees higher than that in surrounding tissue via continuous wave laser illumination of the tumor area (15). U.S. Pat. No. 6,165,440 taught that a combination of radiation and nanoparticles or microparticles could be used to temporarily open pores in cancer cell membranes and blood vessels to allow better penetration of drugs into solid tumors.

U.S. Pat. Nos. 6,530,944 and 6,699,724 disclosed optical diagnostic uses of nanoparticles that emit near-infrared light, i.e., nanodots or absorb near-infrared red light, i.e., nanoshells. Sokolov et al. utilized the capability of gold nanoparticles to reflect light strongly and thereby enhance contrast of abnormal or cancerous tissue specifically targeted with nanoparticles conjugated with monoclonal antibody (16). Oraevsky et al. (17,18) predicted that various nanoparticles can enhance optical absorption in tissue and emit thermoacoustic waves, which in turn can be utilized in optoacoustic imaging of tissue. U.S. Patent Pub. No. 20050175540 described non-spherical nanoparticles and a method by which to optoacoustically detect the presence of objects as small as 1-mm in a body, which can be penetrated by electromagnetic radiation. It was discovered that at least partially metallic nanoparticulates fabricated or manipulated to be non-spherical not only will shift the optical absorption spectrum into the near-infrared range for deeper penetration of radiation into a body, but also will both narrow the absorption band and simultaneously increase the effective absorbance, in certain instances by more than an order of magnitude. This greatly increases the optoacoustic efficacy of the nanoparticulate, making the manipulated nanoparticulate a very high contrast optoacoustic imaging agent.

U.S. Pat. Nos. 5,213,788, 5,411,730, 5,427,767, 5,521,289, 6,048,515, 6,068,857, 6,165,440 06,180,415, 6,344,272, 6,423,056, and 6,428,811 disclose various electromagnetically active nanoparticles for use as therapeutic or imaging contrast agents. It was established by many groups that specific targeting using antibodies increases efficacy of anticancer therapies (19). In addition to IgG type antibodies, short peptides can be used as targeting vectors (20).

It is well recognized that any minimally invasive therapy may benefit from imaging methods that can precisely guide the therapeutic procedure. Lapotko et al. have developed methods of photothermal detection and imaging that enable one to visualize individual cells and thermomechanical processes that occur in cells upon pulsed laser irradiation (21-22). U.S. Pat. Nos. 5,840,023 and 6,309,352 taught a method and a system of optoacoustic imaging that helps detection, localization and real-time monitoring of abnormal tissue in the depth of normal tissue.

Chemotherapy and radiotherapy are often ineffective in treating human cancer, including hematological malignancies, such as leukemia. The state of the art therapy methods and systems have serious limitations, associated with significant treatment toxicity and generation of drug-resistant tumor cells (24-27). The residual cells, therefore, must be eliminated from blood or bone marrow grafts by methods generally called "purging". Available purging methods employ pharmacological and photochemical (PDT) treatment, magnetic and fluorescence based sorting and elimination in cuvette through adsorption to mab attached to its bottom. These methods provide help and relieve to cancer patients, but do not provide sufficient efficacy, i.e. 100% elimination, or adequate speed of cell elimination (28). New treatment strategies that are more effective, faster and less expensive are therefore necessary to overcome these problems.

However, there is a recognized need in the art for an effective and safe method and system that provides selective lysis, i.e., destruction, of targeted abnormal cells and other microstructures or microbodies while leaving all normal cells intact, using electromagnetic radiation. Specifically, the prior art is deficient in therapeutic laser methods and systems utilizing nanoparticulate contrast agents. More specifically, the prior art is deficient in methods and systems of Laser Activated Nano-Thermolysis Cell Elimination Technology (LANTCET) that utilize metal nanoparticles for laser therapy of cancer. The present invention fulfils this longstanding need in the art.

SUMMARY OF THE INVENTION

The present invention is directed to a method for increasing selective therapeutic thermomechanically induced damage to a biological body. The method comprises specifically targeting a biological body comprising a medium with a plurality of nanoparticulates each conjugated to at least one targeting moiety. The nanoparticulates are effective to form one or more nanoparticulate clusters on or in the biological body upon targeting thereto. The biological body is irradiated with at least one pulse of electromagnetic radiation having a spectrum of wavelengths selected to have a peak wavelength that is near to or that matches a peak absorption wavelength of the nanoparticulates. Subsequently, microbubbles are generated from heat produced via absorption of the electromagnetic radiation into the nanoparticulates such that the microbubbles cause selective and increased thermomechanical damage to the targeted biological body. In a related invention the method further may comprise filtering the products of the thermomechanical damage from the medium. In another related invention the method further may comprise receiving a photothermal signal or generating an optical image of thermomechanical effects to monitor and guide selective thermomechanical damage to the biological body.

The present invention also is directed to a system for increasing selective therapeutic thermomechanical damage to cancer cells. The system comprises a chamber containing the cancer cells in a medium, a source of nanoparticulates adapted to specifically target the cancer cells fluidly connected to the cell chamber, an optical chamber adapted to contain the targeted cancer cells fluidly connected to the cell chamber, and a means for filtering out cells damaged by thermomechanical effects resulting from absorption of the electromagnetic radiation emitted at the peak wavelength which is fluidly connected to the cell chamber. A pulsed source of electromagnetic radiation is directed against the targeted cancer cells in the optical chamber, where the source is configured to emit a spectrum of wavelengths selected to have a peak wavelength that is near to or that matches a peak absorption wavelength of the nanoparticulates. In a related invention the system further comprises a means for receiving a photothermal signal or for generating an optical image of the thermomechanical effects.

The present invention is directed further to a method for treating a leukemia in an individual. The method comprises obtaining a sample comprising normal and leukemic cells from the individual and placing the sample in the cell chamber of the system described herein. The cancer cells in the sample are targeted with the nanoparticulates described herein and the targeted cancer cells are irradiated with electromagnetic radiation emitted from the pulsed source comprising the system. The electromagnetic radiation is absorbed by the nanoparticulates thereby causing selective and increased thermomechanical effects damaging to the targeted cancer cells. The damaged cells are filtered out from the sample and the normal cells remaining in the sample are returned to the individual thereby treating the leukemia. The method steps may be repeated zero or more times. In a related invention the method further may comprise receiving a photothermal signal or generating an optical image of thermomechanical effects to monitor and guide selective thermomechanical damage to the biological body. Other and further aspects, features, benefits, and advantages of the present invention will be apparent from the following description of the presently preferred embodiments of the invention given for the purpose of disclosure.

BRIEF DESCRIPTION OF THE DRAWINGS

The appended drawings have been included herein so that the above-recited features, advantages and objects of the invention will become clear and can be understood in detail. These drawings form a part of the specification. It is to be noted, however, that the appended drawings illustrate preferred embodiments of the invention and should not be considered to limit the scope of the invention.

FIGS. 2A-2C show electron microphotographs (FIGS. 2A-2B) of gold nanorods with diameter of 15 nm and 2 different aspect ratios, 3.2 and 6.9, placed on the surface of glass slide, and an experimentally measured optical absorption spectra (FIG. 2C) of these gold nanorods, conjugated with PEG and suspended in water. One can see that a controlled fabrication of relatively monodisperse nanorods with aspect ratio not deviating from the maximum can be achieved. Furthermore, conjugation with PEG slightly changes spectral width and position of the peak absorption.

FIG. 7A is a single K-562 cell directly targeted with nanoparticles with no bubble and no damage at optical fluence of 35 J/cm$^2$. FIG. 7B is a suspension of 30-nm diameter single gold nanoparticles at an optical fluence of 35 J/cm$^2$. FIG. 7C is a single K-562 cell selectively targeted cell, so that clusters of NPs were formed in the cell, optical fluence of 5 J/cm$^2$.

FIG. 9A shows main control cells that were not damaged, i.e., no microbubble-related photothermal response signal was detected from these cells. FIG. 9B shows selectively-targeted cells that were severely damaged, i.e., only cell fragments were found.

FIGS. 10A-10C depict the action of bioconjugated nanoparticulates on normal and tumor cells during LANTCET.

FIGS. 11A-11F depict optical (FIGS. 11A-11B) and fluorescent (FIGS. 11C-11D) images of human leukemia cells (B-lymphocytes) and the fluorescence signal profiles (FIGS. 11E-11F) for those images obtained after incubation at 4° C. (FIG. 11A, 11C, 11E) and 37° C. (FIG. 11B, 11D, 11F). White lines at cell images show the boundaries of nuclei and of outer membranes of the cells.

FIGS. 12A-12H are histograms of fluorescent image parameters showing the maximal values of fluorescent signal in peaks Max (FIGS. 12A-12D) and spatial distribution Mir of fluorescent peaks (FIGS. 12E-12H) for incubation times and temperatures of 37° C., 2 h (FIG. 12A,12E), 37° C., 0.5 h (FIG. 12B, 12F), 4° C., 2 h (FIG. 12C, 12G) and 4° C., 0.5 h (FIG. 12D, 12H).

DETAILED DESCRIPTION OF THE INVENTION

Figure 1A:
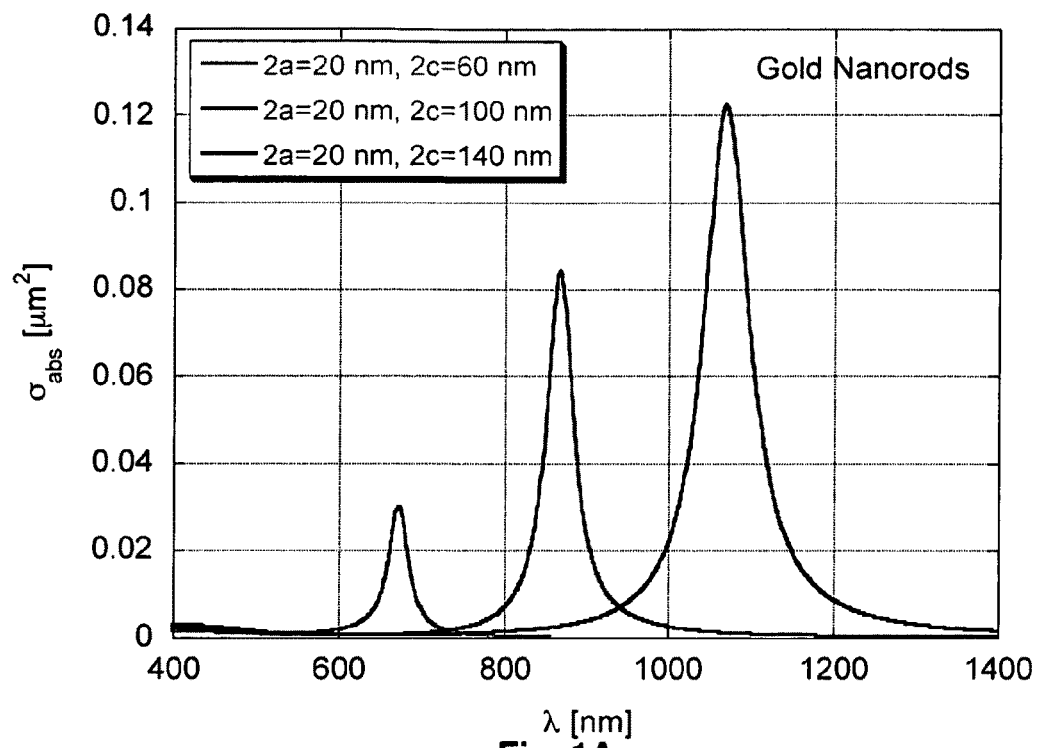
FIGS. 1A-1B show the calculated optical absorption spectra of gold (FIG. 1A) and of silver (FIG. 1B) nanorods. With an increasing aspect ratio, the peak of plasmon resonance absorption gradually shifts to longer wavelengths in the near-infrared.

In one embodiment of the present invention there is provided a method for increasing selective therapeutic thermomechanically induced damage to a biological body, comprising specifically targeting a biological body comprising a medium with a plurality of nanoparticulates each conjugated to at least one targeting moiety, where the nanoparticulates are effective to form one or more nanoparticulate clusters on or in the biological body upon targeting thereto; irradiating the biological body with at least one pulse of electromagnetic radiation having a spectrum of wavelengths selected to have a peak wavelength that is near to or that matches a peak absorption wavelength of the nanoparticulates; and generating microbubbles from heat produced via absorption of the electromagnetic radiation into the nanoparticulates where the microbubbles cause selective and increased thermomechanical damage to the targeted biological body.

Further to this embodiment the method may comprise filtering the products of the thermomechanical damage from the medium. In another further embodiment the method may comprise receiving a photothermal signal or generating an optical image of thermomechanical effects to monitor and guide selective thermomechanical damage to the biological body. In all embodiments the biological body may be an abnormal cell, a bacterium or a virus. In these embodiments the nanoparticulates may have a dimension of about 1 nm to about 1000 nm. Also, the nanoparticulates may be aggregates of nanoparticles. One example of a nanoparticle aggregate comprises spherical nanoparticles. Furthermore, the nanoparticulates may form one or more nanoparticulate clusters. Also, in all embodiments the nanoparticulate may be formed from at least partially metallic nanoparticles, nanorods or nanoshells or may be a carbon nanotube. In one aspect the nanoparticulates are formed from partially metallic nanoparticles that have plasmon resonance absorption of the electromagnetic radiation. In another aspect the nanoparticulates are elongate at least partially metallic nanoparticles. In all embodiments the metal may be gold or silver.

Furthermore, in all embodiments the nanoparticulates comprise a targeting moiety that is a monoclonal antibody or a peptide specifically targeted to a receptor site on the biological body. In an aspect, the receptor site further comprises another monoclonal antibody or peptide attached thereto specific for the targeted monoclonal antibody. Further to all embodiments the nanoparticulates may comprise a surfactant or complementary strands of a nucleic acid conjugated thereto or a combination thereof. In all embodiments the wavelength spectrum of the pulse of electromagnetic radiation may have a range of wavelengths of about 300 nm to about 300 mm. In an aspect the pulse of electricalmagnetic radiation is optical radiation. This optical radiation may have a wavelength in the range from 500 nm to 1150 nm. In all embodiments the pulse of electromagnetic radiation is about 1 ns to about 100 ns.

In another embodiment of the present invention there is provided a system for increasing selective therapeutic thermomechanical damage to cancer cells, comprising a chamber containing the cancer cells in a medium; a source of nanoparticulates adapted to specifically target the cancer cells fluidly connected to the cell chamber; an optical chamber adapted to contain the targeted cancer cells fluidly connected to the cell chamber; a pulsed source of electromagnetic radiation directed against the targeted cancer cells in the optical chamber, where the source is configured to emit a spectrum of wavelengths selected to have a peak wavelength that is near to or that matches a peak absorption wavelength of the nanoparticulates; and means for filtering out cells damaged by thermomechanical effects resulting from absorption of the electromagnetic radiation emitted at the peak wavelength, where the filtering means is fluidly connected to the cell chamber. In a further embodiment the system comprises a means for receiving a photothermal signal or for generating an optical image of the thermomechanical effects.

In these embodiments the nanoparticulates each comprise at least one targeting moiety specifically targeted to a receptor site on the cancer cell. Furthermore, the receptor site may comprise another targeting moiety attached thereto which is specific for the targeting moiety on the nanoparticulates. Examples of a targeting moiety are a monoclonal antibody or a peptide. In another further embodiment the nanoparticulates further may comprise a surfactant or complementary strands of a nucleic acid conjugated thereto or a combination thereof.

In all embodiments the cancer cells may be leukemic cancer cells. Also, in all embodiments the dimensions, shapes, or metal or carbon compositions of the nanoparticulates, aggregates of nanoparticles or nanoparticulate clusters are as described supra. Furthermore, the spectrum wavelengths and types of electromagnetic radiation and time of pulse duration are as described supra.

In yet another embodiment of the present invention there is provided a method for treating a leukemia in an individual, comprising obtaining a sample comprising normal and leukemic cells from the individual; placing the sample in the cell chamber of the system described supra; targeting the cancer cells in the sample with the nanoparticulates comprising the system; irradiating the targeted cancer cells with electromagnetic radiation emitted from the pulsed source comprising the system, where the electromagnetic radiation absorbed by the nanoparticulates causes selective and increased thermomechanical effects damaging to the targeted cancer cells; filtering out the damaged cells from the sample; returning the normal cells remaining in the sample to the individual thereby treating the leukemia; and repeating the method steps zero or more times.

In a further embodiment the method comprises receiving a photothermal signal or generating an optical image of the thermomechanical effects to monitor and guide selective thermomechanical damage to the cancer cells. In both embodiments the thermomechanical effects are caused by heat generated within the nanoparticulates from absorbed electromagnetic radiation sufficient to form microbubbles in the cancer cells.

As used herein, the term, "a" or "an" may mean one or more. As used herein in the claim(s), when used in conjunction with the word "comprising", the words "a" or "an" may mean one or more than one. As used herein "another" or "other" may mean at least a second or more of the same or different claim element or components thereof. As used herein, the term "nanothermolysis" refers to damage, ablation, destruction of biological target cells assisted and enabled by nanoparticles. As used herein, the phrase "Laser Activated Nano-Thermolysis" refers to selective damage of cells using nanoparticles (nanoparticles) targeted to specific receptors expressed in cancer cells, but not in normal cells. As used herein, the phrase "Cell Elimination" refers to a successful treatment procedure. Thus, as used herein, the phrase "Laser Activated NanoThermolysis Cell Elimination Technology" or "LANTCET" refers to a method and a system for electromagnetic radiation induced selective destruction of abnormal biological structures utilizing bioconjugated nanoparticles, such as tissues, cells, bacteria and viruses. As used herein, the term "nanoparticulate" refers to a single nanoparticle, a collection of nanoparticles, or a nanoparticle aggregate. As used herein, the term "nanoparticulate cluster" describes specific aggregation of nanoparticles in which nanoparticles may touch each other or be in proximity to each other, so that when irradiated with laser pulses or other pulses of electromagnetic energy, they present themselves as a single unresolved source of thermal energy. As used herein, the phrase "at least partially metallic" refers to a preferred nanoparticulate effective to absorb electromagnetic radiation by the plasmon resonance mechanism, which is known to yield very strong absorption coefficient.

Provided herein are methods and systems using Laser Activated Nano-Thermolysis Cell Elimination Technology or LANTCET for the electromagnetic radiation induced selective destruction and purging of abnormal biological structures, such as tissues, cells, bacteria and viruses. LANTCET has advantages over current methods of purging as shown in Table 1.

TABLE 1

| Method | Magnetic separators | Flow Cytometry | PDT | LANTCET |
|---|---|---|---|---|
| Rate, cell/s | $10^7$ | $10^4$ | $10^7$ | $10^7$ |
| Volume, ml per one cycle | 50-100 | 50 | >1000 | >1000 |
| Max amount of treated cells | $10^9$ | $10^6$ | $10^{10}$ | $10^{10}$ |
| Efficacy, % of labeled cells | 90 | 99.9 | 95 | 99.9 |
| Safety | Additional chemical treatment of the cells for removing magnetic particles may damage normal cells | Potential cell damage at high rate | Potentially toxic for normal cells | Potential laser damage to 0.1-3% of normal cells |

Although magnetic elimination is not damaging to normal cells, its main disadvantage is that efficacy of this method is not sufficient for purging residual cancer cells due to a lack of strong magnetic force that separates small ferrous beads coupled to the target cells from normal untargeted cells. The main advantage of flow cytometry is its high efficiency of cell sorting, however, the low throughput of this method is a limiting factor. Photodynamic therapy lacks sufficient specificity to target cells due to low contrast provided by organic dyes. Overall, these methods and systems lack means for high through-put that is effective, specific for the target cells and safe.

In a LANTCET method, strongly absorbing nanoparticles provide contrast relative to untargeted cells that is unmatched by any other contrast agent. Furthermore, formation of clusters of nanoparticles in cells makes laser thermolysis of the target cells by microbubbles a very effective, low threshold process that is harmless to normal untargeted cells. Selectivity is conferred by targeting an abnormal biological structure with bioconjugated nanoparticles. These nanoparticles are targeted to molecular receptors on the surface of the target cells using antibodies, such as immunoglobulin type proteins or short peptides, which help to achieve selectivity of nanoparticle accumulation in cells.

The targeting protocol is designed to produce clusters of nanoparticles on the surface of cells and/or inside the abnormal cells in order to enhance efficacy of thermomechanical interactions of electromagnetic radiation with the nanoparticles. Such enhancement results in a substantially lower threshold of the fluence or the power required to achieve the abnormal cell damage. This in turn increases specificity and probability of damage to the targeted cell damage and of safety to normal cells and tissues. The methods and systems described herein have a variety of applications including, but not limited to, minimally invasive therapy of cancer, such as eliminating early subsurface tumors from tissue and purging leukemia cells from bone marrow graft transplants or blood.

Generally, the methods and systems described herein are effective to substantially increase the thermomechanical damage to a biological body or microbody or microstructure, such as, but not limited to, a biological cell, a bacterium, or a virus resulting from a pulse of electromagnetic radiation absorbed by the nanoparticles and to decrease the damage to the surrounding normal body decreased. More particularly, the methods and systems described herein include the following components and steps.

Nanoparticles

The nanoparticulates provided herein are designed with the maximum capability to absorb electromagnetic radiation of a wavelength effective to penetrate the body, but not to be absorbed by molecular content of the body. That is, the nanoparticulates must absorb electromagnetic radiation very strongly, so that such absorption is sufficient to superheat them well above the boiling point of the surrounding biological medium, e.g., water or a water like medium, with a fluence of energy that produces insignificant direct heating of the surrounding medium. Nanoparticles that strongly absorb electromagnetic radiation in the near-infrared spectral range, the range of wavelengths where molecular constituents of biological cells and tissues possess no or minimum absorption are used. Preferably, the nanoparticles may be at least partially metal nanoshells, metal nanorods or carbon nanotubes.

One skilled in the art can predict that many combinations and complex structures can be created based on basic properties of nanoparticles known in the art. It is contemplated that clusters of other nanoparticles, such as carbon nanotubes and liposomes filled with organic dyes, can be utilized for LANTCET since clusters of these particles can strongly absorb near-infrared radiation. Although, the near-infrared spectral range seems to be the preferred range based on what is known in the art, nanoparticles may be designed to absorb x-rays, microwave (RF) radiation or visible radiation. The absolute value of the absorption coefficient for a given wavelength of electromagnetic radiation is not as important as the contrast, that is, difference, ratio between the absorption coefficient in the nanoparticulate and the background surrounding medium or body that was not targeted with said nanoparticulate.

The most preferred materials for nanoparticulate composition are gold and silver and the most preferred shape of the nanoparticulate is an elongated asymmetric shape, such as nanorods or more complex structures involving nanorods, such as nanostars and nanourchins. However, a symmetric composition, such as spherical, particles are not excluded. For example, nanorods with aspect ratio close to one are spheres, which have peak optical absorption in the green spectral range. Formed nanoparticulate clusters may be spherical or aspherical in three-dimensional space, the formed shape may be fractal or chaotic and may be a combination of various aggregate shapes and structures.

The most optimal nanoparticles in terms of maximum absorption in the near-infrared spectral range are the silver nanorods. Also, silver nanorods or more complex elongated silver nanostructures can be designed to absorb near-infrared very strongly, i.e., with an absorption cross-section up to 100 times the physical cross-section. However, silver is not a completely inert metal and can be toxic to normal cells, if used in large concentration. The most optimal nanoparticles in terms of minimal toxicity in the absence of radiation are gold nanoparticles. Furthermore, gold nanorods or more complex structures encompassing gold nanorods, such as gold nanostars or nanourchins, can be designed to absorb near-infrared very strongly such that the absorption cross-section exceeds the physical cross-section several times over, next only to silver nanostructures.

The dimensions of the nanoparticulate are determined from its size which must be sufficiently small to be suspended in a water solution of an appropriate surfactant, e.g., PEG, as compared to pores in biological tissues and blood vessels, so that the nanoparticulate can diffuse through tissue and to be effectively endocytosed by cells, and so that effective targeting of nanoparticles to cell receptors can be accomplished. The size of the nanoparticle must effective for absorbing electromagnetic radiation of chosen wavelength due to plasmon resonance, which requires that the maximum characteristic dimension of the nanoparticulate will be smaller than the wavelength. Some nonmetallic nanoparticles, such as semiconductor carbon nanotubes do not have limitation of size for absorption, but any one skilled in the art of radiation absorption can conclude that there is an optimal size of any particle beyond which absorption of radiation will be less effective and less homogeneous inside the particle. Thus, the nanoparticulate must be no smaller than 1-2 nm and no larger than 1000 nanometers. Nanoparticulate clusters, also provided by the instant invention, may be larger than a single nanoparticulate, i.e. have dimensions of up to several microns.

A preferred nanoparticulate is a partially metallic nanoparticulate with an elongated shape, i.e. with an aspect ratio greater than 1, which may be a collection of nanoparticles. A non-spherical nanoparticulate comprising a nanoparticle aggregate does not require that the nanoparticles of the aggregate be non-spherical. The nanoparticles of the aggregate may comprise spherical nanoparticles ordered in a structure to have the properties of the nanoparticulate disclosed herein.

Particularly, a nanoparticulate aggregate is so ordered and the nanoparticles are at least partially coated with an organic material suitably comprising complementary molecules with high affinity to each other to ordain such order. For example, a collection of spherical nanoparticles may be aggregated as an elongated nanoparticulate, which shift their optical absorption as a function of the aspect ratio, i.e. ratio of small axis length to long axis length. One example of elongated nanoparticulate is gold or silver nanorods. One skilled in the art can appreciate that these types of nanoparticulates have tunable absorption in the near-infrared spectrum of electromagnetic radiation and that their absorption peaks are narrow and very strong, i.e., much stronger than those of biological molecules. These properties are beneficial for application in the Laser Activated Nano-Thermolysis Cell Elimination Technology.

A nanoparticulate used in this invention may be combinations of nanoparticles of one shape with nanoparticles of another shape to form nanoparticulate geometries effective to absorb a selected specific wavelength or range of wavelengths and further form nanoparticulate clusters, which help to produce microbubbles within target cells, which in turn produce maximum thermomechanical damage by laser or other electromagnetic pulses. Thus, for medical or biological applications the details of both dimension and shape are important to LANTCET, since these parameters enable efficient accumulation of nanoparticulate clusters in the target body, such as abnormal biological cell.

The nanoparticulate may be at least partially metallic" and be effective to absorb electromagnetic radiation by the plasmon resonance mechanism. Alternatively, the present invention encompasses nanoparticles, such as carbon nanotubes, that possess properties of semiconductors and yet have very strong optical absorption at various wavelengths of electromagnetic radiation. Either are effective in the LANTCET methods and systems described herein.

Bioconjugation

The present invention encompasses the use of nanoparticles or aggregates of nanoparticles that are conjugated with biological, i.e., organic material. The purpose of such bioconjugation is to (i) produce nanoparticulates that are well suspended in water, (ii) to target specific receptors in abnormal cells and (iii) to form clusters of nanoparticles inside cells or on the cell surface, but not outside the cells in suspension. It is desirable that the nanoparticles have multiple molecules conjugated to their surfaces to optimize the biological and chemical properties of the particles and to maximize the desired formation of clusters inside target cells, but not to form aggregates outside the cells. Coated metal, partially metal and nonmetal nanoparticles or aggregates of these nanoparticles as contrast agents for laser activated nanothermolysis, i.e. selective thermomechanical damage to target abnormal cells, may be used.

Conjugated nanoparticles may have coatings that are covalently bound to the surface of the particles and/or coatings that physically adhere to the surface of the particles. One bond used most frequently in conjugation of gold and other metals to biological molecules is a dative S=bond provided by the thiol —SH group or sulfhydryl group. U.S. Pat. Nos. 6,821,730, 6,689,338 and 6,315,978 and others (29-34) teach methods of nanoparticle bioconjugation for a variety of biomedical applications. One skilled in the art may predict that numerous techniques exist to conjugate nanoparticles with biological molecules so that such conjugation is chemically stable upon administration of said nanoparticulates in vitro and in vivo. Such conjugated nanoparticulate also must be nontoxic in the absence of radiation and be unrecogniseable as foreign by the human (or animal) immune system to protect them from being scavenged by the immune system before they reach the target body.

In addition proteins or other biological molecules may be used as surfactants. Particularly desirable surfactants are block copolymers, especially block copolymers in which one block is polyethyleneglycol (PEG) (35). PEG can be labeled bi-functionally on opposite sides of the polymer. One side is usually labeled with a thiol or SH group to have strong affinity to metals, especially gold. The opposite side is usually labeled with an $NH_2$ group, which permits convenient conjugation of proteins, such as a monoclonal antibody. PEG, in having hydrophilic groups on the outside of the polymer, prevents nanoparticles from being recognized by neutrophils, macrophages and other scavengers in the circulation or in the mixture of blood cells. The invention further encompasses the use of a nanoparticulate comprising nanoparticles that are stabilized against uptake by the reticuloendothelial system using appropriate surfactants or other particle coatings.

Another purpose of the surfactants or other substances used to coat the particles is to prevent particle aggregation outside the target cells. Aggregation of the individual particles would lead to particle growth and to precipitation of the particles from the suspension that would shorten the shelf life of any conjugate formulation. The instant invention encompasses the use of bioconjugates that are stabilized against particle aggregation and precipitation through the use of surfactants or other particle coatings. Optionally, the surfactant may serve as a platform for the attachment of other chemical species with desirable biological or chemical properties, which may help to form clusters of nanoparticles inside the target cells. For this purpose, a surfactant or other surface-active agent with reactive functional groups is desirable. As a result, both the surfactant and the attachment site should have reactive functional groups. An optional spacer or linker also should have a pair of reactive functional groups.

An enabling component of nanoparticulate bioconjugates is a targeting vector or moiety. The targeting vectors or moieties may be antibody protein, protein fragments, short peptides or other molecules with a strong or high affinity to target receptors and no or little affinity to target other biological molecules on or in the surrounding medium or body. Regardless of whether the targeting vectors adhere directly to the surface of the nanoparticle or is attached indirectly through the surfactant, the specific receptors for the targeting vectors may be chemical groups, proteins, or other species that are overexpressed by abnormal target tissue or cells. Generally, the receptors may be any chemical or biochemical feature of tissue or cell type to be treated and eliminated. In addition the nanoparticles may be conjugated to a secondary vector or moiety, for example, an antibody or peptide having high and specific affinity to the primary vectors. Such secondary antibody may help to produce aggregates of nanoparticles around the primary targeted nanoparticles on the cell surface.

Specific antibodies for targeting leukemia or other tumor cells for elimination of these tumor cells from the body, such as bone marrow transplants), depend on the type of cells being targeted. Examples include, but are not limited to CD33 and CD123 for acute myeloid leukemia (AML), CD20 for chronic lymphocytic leukemia (CLL), or CD19, CD20 and CD22 for acute lymphoblastic leukemia (ALL).

In addition to successful targeting, clusterization of accumulated nanoparticles in cells of interest must occur. Preferred clusters are two- and three-dimensional structures comprising even numbers of elongated nanoparticles, e.g., two- and three-dimensional stars pyramids or other such structures. Methods for organizing metal nanoparticles into stabilized clusters of aggregates are well-known. For example, covering the surface of different gold particles with complementary strands of DNA favors the self-assembly of the particles into ordered aggregates (36-38). Aggregate formation results from the favorable interaction between the complementary strands of DNA. The instant invention encompasses the use of contrast agents for optoacoustic imaging comprising aggregates of particles coated with complementary strands of artificial or natural DNA, RNA or analogs of RNA or DNA.

Preferably, the nanoparticulate comprises aggregates of metal particles. Such aggregates exhibit a collective plasmon resonance that enhances the total accumulated thermal energy over that expected for single particles in proportion to the total volume of a cluster. Furthermore, clusters of metal nanoparticles can exhibit collective resonance absorption, which is stronger than a simple additive of the optical absorption by single particles (39). For example, a cubic stack of 16 nanorods of 4 layers with 4 nanorods in each layer will absorb more optical radiation than 16 separate nanorods. The presence of a collective plasmon resonance for a collection of nanoparticles is evidenced experimentally by a non-linear increase in the intensity of the optoacoustic signal as the particle concentration increases and aggregates are formed.

A useful biochemical means of promoting controlled particle aggregation is to coat different particles with complementary sequences of nucleic acids, referred to as nucleotides, oligo- and polynucleotides, including deoxyribonucleic acid (DNA) and ribonucleic acid (RNA). Physical means also may be used to promote aggregation, e.g. heating of the nanoparticulates with infrared light (40). Elevated temperature also promotes endocytosis. The endocytosis may be enhanced using an internalizing mab (40).

Stimulated Clusterization

A cluster of strongly absorbing nanoparticles must be formed in order to produce effective local thermomechanical effect, such as generation of an expanding vapor bubble. The cluster has a characteristic dimension, D, comprising small particles with a characteristic dimension, d. A single large particle with a characteristic dimension, D, is not effective as the laser-activated target because of several limitations.

First, large single metal particles do not absorb laser radiation as strongly as a group of smaller nanoparticles because Plasmon resonance interactions are limited to nanoparticles much smaller than the wavelength of electromagnetic radiation. The near-infrared radiation 650-1150 nm penetrates cells with minimum absorption, thus being the most beneficial for selective laser treatment. Nanoparticles that are much smaller than 650-1150 nm are in the range of 10-250 nm, will possess maximum absorption per particle, but are too small to generate vapor bubbles at the temperature of $\Delta T=100°$ C., i.e., the temperature of adiabatic vaporization.

A large particle made of organic dyes, polymers or other absorbing materials, can be used to generate vapor bubble at the temperature of 100° C.:

$$\Delta T = \mu_a F/\rho C = 100° C. \quad (1),$$

where $\mu_a$ is the optical absorption coefficient, F is the laser fluence, $\rho$ is the nanoparticle density, and C is the heat capacity of the nanoparticle material. However, due to relatively low absorption of these particles, a very high laser fluence, F, is required to reach 100° C. in these particles. Such high laser fluence is not safe for normal cells and selectivity of the treatment would be lost.

Secondly, large and strongly absorbing particles also are not effective as a contrast agent, because these particles can not be effectively targeted to cells. The efficiency of targeting is roughly inversely proportional to the particle size. This is explained easily because a large particle cannot be held strongly by a single chemical bond formed between the antibody and the receptor. Also, large particles can not be effectively conjugated to vector molecules, such as monoclonal antibodies or peptides, specific to receptors of abnormal cells. Large particles also are very hard to keep in water suspension with no sedimentation at the bottom of the cuvette. Large particles also will not penetrate through tissues in case their target is not on the very surface.

Clusterization of nanoparticles on and in target cells occurs due to specially designed targeting procedure, which utilizes complementary molecules and high affinity molecular reactions to increase probability of nanoparticle-nanoparticle interaction in cells. The strength of nanoparticle-cell receptor interactions is also maximized by choice of monoclonal antibody. In addition conditions of time duration of targeting, temperature of the body to be targeted, concentration of nanoparticles, and conditions of cellular internalization process or endocytosis must be optimized in order to achieve maximum rate of nanoparticle clusterization. The efficacy of clusterization can be represented as a bell-shaped function of each of these quantitative conditions. One of ordinary skill in the art of cell biology can appreciate that the specific optimal conditions depend on specific medical application.

Various general methods known in the art (33-41) may be used to stimulate clusterization of nanoparticulates in the body. A site of interest, e.g., a tumor cell or tissue comprising the same, may be pretreated with a monoclonal antibody having multiple binding sites is targeted with nanoparticles conjugated to a secondary monoclonal antibody specific for the first monoclonal antibody. Alternatively, nanoparticles conjugated with a primary antibody are targeted to the site of interest followed by targeting nanoparticles conjugated to a second monoclonal antibody to the first monoclonal antibody.

In another alternative method, nanoparticles conjugated to a primary monoclonal antibody and further conjugated to a first aggregating molecule, such as biotin, are targeted to a site of interest. Subsequently, nanoparticles conjugated with the primary monoclonal antibody and further conjugated to a second aggregating molecule, such as streptavidin, are targeted to the avidin-linked nanoparticles. The use of the first and the second aggregating molecules that have high affinity to each other is not limited to biotin-streptavidin linking. One of ordinary skill in the art would be familiar with a variety of complementary chemical or biochemical compounds or compositions that have a very strong affinity to each other, for example, but not limited to, adenine-thymine and guanine-cytosine nucleotides, protein A or immunoglobulin. Furthermore, stimulation of clusterization inside target cells may be accomplished by using an internalizing monoclonal antibody.

A two-stage targeting method, which provides delivery and clusterization of the nanoparticles inside the target cell also is provided. At the first stage, a high concentration of nanoparticles is provided at the outer cell membrane using monoclonal antibodies and specific staining conditions to prevent endocytosis of nanoparticles inside the cell, which is being maintained at a low temperature of 4° C. At the second stage, after washing out unbound nanoparticles from the cell suspension the temperature is raised to 37° C. for an optimal time interval of about 30 min to stimulate the process of endocytosis. The nanoparticles are delivered thereby from the cell outer membrane to inside the cell by endocytosis, including formation of vesicles at the cell membrane. Several nanoparticles in proximity to each other will then be captured at the cell membrane by emerging vesicles, which then deliver nanoparticles inside the cell. As a result, the nanoparticles are concentrated spatially within the vesicles and their spatial distribution inside the cell represents the clusters. Vesicles may exist in the cells for a long time, which to allows further stages of LANTCET to be performed. Also vesicles may deliver nanoparticles to other specific cell compartments where further concentration of nanoparticles may occur.

This protocol can be applied to any type of cell because endocytosis is a universal transport mechanism and vesicles will emerge in any type of cell. The occurrence of the nanoparticulate clusters in the target cells as well as single nanoparticles can be visualized by electron microscopy (44). To avoid nonspecific targeting of normal bodies or microstructures, such as cells), the temperature in the targeting chamber is preferably reduced to 4° C. It is demonstrated herein that minimal or no accumulation of nanoparticles occurred in cells having no specific receptors for targeting vectors used.

Administration of Nanoparticles

The methods and system provided herein are applicable to animal or non-animal bodies, such as cancer cells or bacteria. Thus, without limitation, in terms of medical significance, for example, the body may be an in vivo or in vitro specimen and the object may be a molecule or a virus or bacterium. Alternatively, the body may be an ex vivo specimen, such as a disseminated cancer cell, for example a leukemic cell. The body animate may be an animate human or non human and the object may be biological and comprise a specific tissue, cell or microorganism. For example, the object detected may be a tumor in an animate human or a specific cell or virus harmful to the human.

The abnormal body or a cell, which is the subject of LANTCET treatment with the goal of elimination, may be pretreated by specific primary monoclonal antibodies or other vectors that can be further used as receptors for secondary monoclonal antibodies or other vectors in order to form clusters of nanoparticulates in the abnormal body. Those skilled in the art can recognize that a targeting vector against cancer receptor may be used not only for selective delivery of nanoparticles to the target body, but also for direct therapeutic purposes. Such conclusion comes with understanding that targeting vectors, such as monoclonal antibodies, attached to protein receptors on the surface of cancer cells may disable vital functions of those receptors and thereby kill those cancer cells.

An example of such therapeutic action is the monoclonal antibody, trastuzumab, commercially known as HERCEPTIN, raised against receptors associated with HER2/neu gene overexpressed in breast cancer cells and other types of cancer. HERCEPTIN has been successfully used for treatment of metastatic breast cancer (42). As disclosed herein, Laser Activated Nanothermolysis of abnormal cells may be enhanced by pretreatment of the target cells with primary monoclonal antibodies or primary vectors raised against vital receptors on target cells. In association with previously disclosed therapeutic effect of targeting vectors, it is contemplated that the nanoparticulates disclosed in this invention also can be used as an anticancer therapeutic agent. In addition, the designed nanoparticulate can contain an agent molecule to enhance toxicity of such nanoparticulate to tumor cells. Such addition is most desirable if the targeting protocol permits absence of the nanoparticulate accumulation in normal cells.

For imaging a human or a non-human body, many modes of application are possible, depending on the therapeutic requirements. Administration of the therapeutic agent can be systemic or local. Administration can be made intravenously, orally, topically or through direct application of the agent to human or non-human tissue or cells. Local administration of the nanoparticulate agent may be by topical application, by means of a catheter, with a suppository, or by means of an implant or by mixing the nanoparticulate with target bodies (cells) in vitro. Other means of local application will be apparent to those skilled in the art.

Furthermore, the contrast agents may be administered in conjunction with a hyperthermic application, that is, the artificial elevation of the local temperature of an organ or another body part. Hyperthermia accelerates the passage of nanoparticles through the capillaries of the vascular system of growing tumors (43). Hyperthermia also will enhance the uptake of the nanoparticulate by other types of diseased tissue and cells through widening pores and channels in cell membranes.

Any of the many different means of elevating temperature are possible. These include, but are not limited to, the application of thermostatic chambers, the use of focused ultrasound, microwave or RF irradiation. Any or all of these heating procedures can be actively applied while the contrast agent is applied, or, alternatively, the heating can take place up to 24 hours prior to the administration of the agent.

Electromagnetic Radiation

A nanoparticulate is administered to a medium surrounding the body for treatment of the body. Preferably, the nanoparticulate is at least partially metallic, has a formed non-spherical shape having a minimal characteristic dimension in the range from about 1 to about 1000 nanometers and has a formed composition capable of absorbing the electromagnetic radiation and of accumulating thermal energy either in the nanoparticulate or in the body greater than the irradiated body could produce in the absence of the nanoparticulate.

In accordance with the invention, electromagnetic radiation is directed onto the body. The electromagnetic radiation has a specific wavelength or spectrum of wavelengths in the range of about 1 nm to about 1 m which encompasses X-rays to radiofrequency. More preferably, the range is about 300 nm to about 300 mm selected so that the wavelength or wavelength spectrum is longer by a factor of at least 3 than the minimum characteristic dimension of the nanoparticulate. Even more preferably, the spectral range is from green (520 nm) to infrared (1120 nm) wavelengths which can be produced by commercially available lasers. Most preferably, the range of wavelengths is in the near-infrared from about 650 nm to about 900 nm, where tissue and cells have absolutely minimal optical absorption and scattering within which the most preferred gold and silver nanoparticles possess maximum absorption cross-section.

The nanoparticulate made of elongated nanoparticles absorbs the electromagnetic radiation more than would one or more non-aggregated spherically shaped particles of the same total volume with a composition identical to the nanoparticulate. The nanoparticulate by such absorption produces an enhanced thermomechanical effect resulting from the absorption.

The most effective and safe LANTCET procedure can be performed with electromagnetic irradiation of a wavelength that generates microbubbles around nanoparticulate clusters with minimal fluence, i.e., energy per irradiated area, in the targeted body. The irradiation can be generated with a laser, but the invention encompasses the use of any radiation source, regardless of its source. Examples of alternate radiation sources include, but are not limited to, flash lamps, incandescent sources, magnetrons, radioactive substances, or x-ray tubes. The invention encompasses the use in LANTCET of nanoparticulates comprising metal particles or aggregates of metal with electromagnetic irradiation having a wavelength matching the wavelength of peak absorption in the nanoparticulates.

Advantageously, the nanoparticles comprise gold or silver and the wavelength for irradiation is about 520 nanometers to about 1120 nanometers. For example, the wavelength for irradiation is about 520 nanometers to about 1120 nanometers and the nanoparticles in a collection are at least partially gold or silver, are elongated in at least one dimension and have an aspect ratio of at least 2.0. Alternatively, the wavelength for irradiation is about 520 nanometers to about 1120 nanometers, the nanoparticles in a collection are at least partially gold or silver, are elongated, and have a bimodal distribution of aspect ratios. Particularly, one local maximum in the distribution of aspect ratios is about 4 and the other local maximum in the distribution of aspect ratios is about 7. In a multimodal distribution of aspect ratios, the electromagnetic radiation comprises two or more wavelength spreads. In an example for a bimodal distribution of aspect ratios of elongate at least partially gold nanoparticles, one wavelength band is about 690 nanometers to about 800 nanometers and another wavelength band is about 800 nanometers to about 1120 nanometers. Alternatively, the same wavelength range is used and the nanoparticulate is a carbon nanotube, preferably a single wall carbon nanotube.

In a partially metallic nanoparticulate, heating thereof is produced preferably through plasmon derived resonance absorption by conductive electrons in the nanoparticulates. Suitably, the electromagnetic radiation used is pulsed and is emitted from a pulsing laser operating in the near-infrared spectral range. Interaction of nanoparticles with the body being detected produces a shift of the absorption maximum by the nanoparticles for the selected wavelength or spread of wavelengths.

Interaction of Electromagnetic Pulses with Nanoparticles of Various Sizes

Preferably, LANTCET utilizes elongated gold or silver nanoparticles with an absorption peak in the near-infrared, i.e., 620-1120 nm, the most suitable spectral range for deep tissue imaging due to the relative transparency of tissues to near-infrared light. Gold nanoellipsoids or elongated nanoprisms, nanoshells, and other metal nanoparticles absorbing in the NIR can be produced in limited quantities in the laboratory (45-47). Therefore, commercially available spherical nanoparticles as a nanoparticulate are used to demonstrate the feasibility of selective ablation of tumor cells using laser activated nano-thermolysis. The disclosure provided herein will allow one of ordinary skill in the art to predict changes in the results of LANTCET for various nanoparticles based on their optical and thermal properties, shape and dimensions.

Figure 1B:
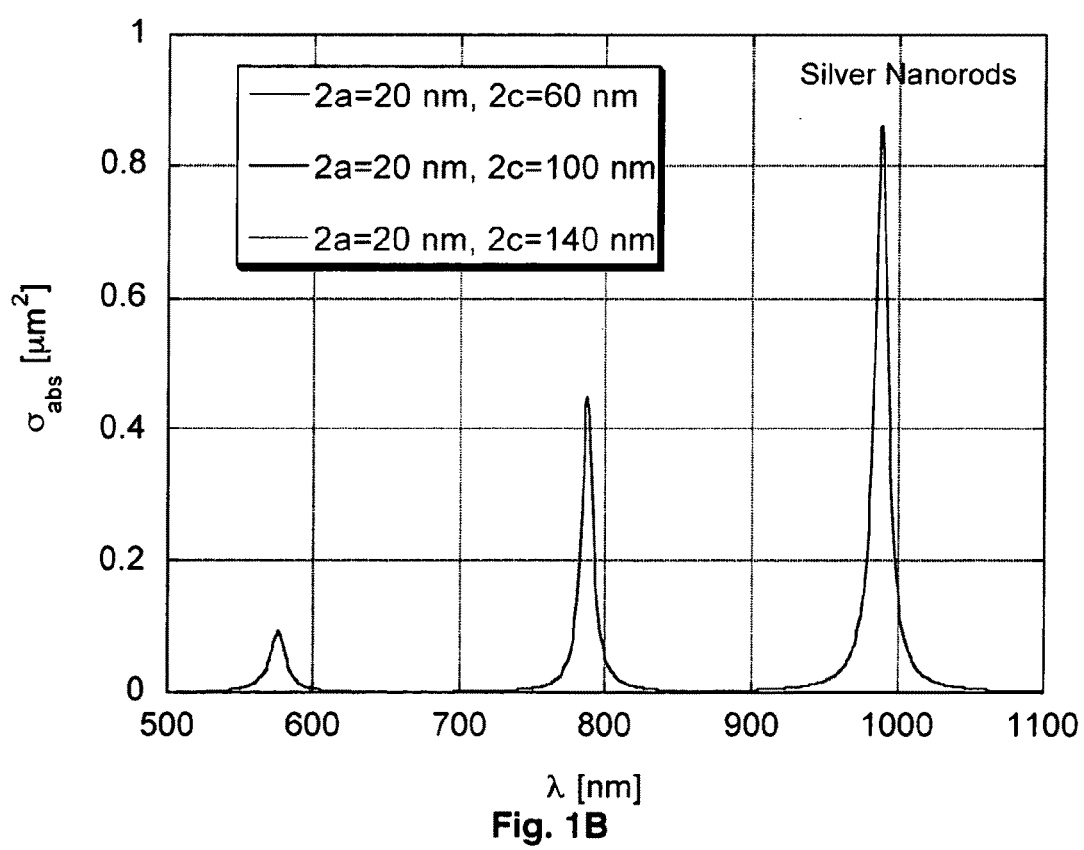

FIGS. 1A-1B show the absorption cross-section for gold and silver nanoellipsoids (nanorods) as a function of their diameter employing formulas described in detail elsewhere (39). One of ordinary skill in the art can appreciate that the total optical energy absorbed by a nanoellipsoid increases initially as a cube of the diameter, that is, proportional to the volume of these nanoparticles, and then increases as a square of the diameter, that is, proportional to the area of the nanoparticles.

Superheating of the nanoparticle, which evaporates a layer of surrounding water, may produce a microbubble. Surprisingly, it was discovered herein that microbubbles cannot be produced around small nanoparticles, such as about 10 μm to about 100 nm, using optical fluence that heats these nanoparticles up to 100° C., the boiling point of water, and even up to 374° C., the critical temperature of water. Even with extremely high fluence of pulsed electromagnetic radiation, only nanobubbles invisible by optical microscopy can be produced. With a further increase of absorbed energy, the small nanoparticles evaporate and disappear from aqueous suspension. Even for larger nanoparticles (>100 nm) it is statistically difficult to produce visible microbubbles.

The reason for such phenomenon is that a nanoparticle with small volume can accumulate only a limited amount of thermal energy, not sufficient to evaporate a volume of water required to produce a microbubble that can sustain in suspension for a measurable time. There are two major physical reasons for such effect. First, strong surface tension that is inversely proportional to the bubble radius makes the surface tension force very strong for bubbles smaller than certain radius. Secondly, viscosity of water provides an extremely strong force on small nanobubbles thereby preventing their growth to microbubbles. Thus, only when the nanoparticulate cluster has sufficient size and mass to accumulate the thermal energy from electromagnetic radiation, is it possible to generate microbubbles of vapor using energy fluence that heats the nanoparticulate cluster to a temperature between 100° C. and 374° C. This energy fluence under optimal experimental conditions can be safe for normal cells. In the absence of nanoparticle clusters, the required energy fluence will be much higher than 1 J/cm$^2$, which is not safe for normal cells.

Using the known absolute values for gold nanoparticle absorbance along with the thermal diffusion models for different shapes of heated objects (48), an estimate can be made of the minimum laser fluence required to heat a nanoparticle or a nanoparticulate cluster up to a boiling point of water at 100° C. or a critical point of water around 374° C. Upon irradiation with a laser pulse, heat diffusion within a gold nanoparticle occurs on the scale of picoseconds. Therefore, gold nanoparticles will be homogeneously heated with a 5 ns to 50 ns pulse width of a typical Q-switched laser suitable for LANTCET.

Heat diffusion time is the time required for the transfer of about ⅔ of the thermal energy stored in a nanoparticle to the surrounding medium. The heat diffusion time from a nanoparticle or a cluster of nanoparticles to the surrounding water occurs on the scale of sub-nanoseconds to tens of nanoseconds, depending on the size of a nanoparticule, d, being heated by radiation, and its shape (48):

$$\tau_{HD} = \frac{d^2}{24\chi}, \text{ if the shape is spherical} \quad \text{(eq. 2a)}$$

$$\tau_{HD} = \frac{d^2}{16\chi}, \text{ if the shape is cylindrical} \quad \text{(eq. 2b)}$$

$$\tau_{HD} = \frac{d^2}{4\chi}, \text{ if the nanoparticulate cluster is shaped as disk} \quad \text{(eq. 2c)}$$

In the formulas (2a-2b-2c), $\chi=1.3\cdot10^{-3}$ cm$^2$/s is the thermal diffusivity of water at room temperature. The expression describing the increase of temperature of the nanoparticle during laser pulse, i.e. when the particle simultaneously absorbs light and diffuses heat) can be presented in the following fashion (13):

$$\Delta T_{NP} = \frac{F\sigma_a^{NP}}{V_{NP}\rho_{NP}C_{NP}} \times \left(\frac{\tau_{HD}}{\tau_L}\right) \times \left[1 - \exp\left(-\frac{\tau_L}{\tau_{HD}}\right)\right] \quad \text{(eq. 3)}$$

where F[mJ/cm$^2$] is the incident (upon the nanoparticle) laser fluence and $\sigma_a^{NP}$ is the plasmon-derived absorption by the spherical gold nanoparticle at the wavelength of laser irradiation, $V_{NP}$ is the volume of nanoparticle being irradiated, $\rho_{NP}$, is the density of nanoparticle material (for gold $\rho_g$=19.3 g 1 ml), $C_{NP}$ is the heat capacity of nanoparticle material (for gold $C_g$=0.128 J/g ° K.), $\tau_{HD}$ is the effective heat diffusion time from gold into water (surrounding medium). As formula (3) indicates, for effective utilization of the electromagnetic pulse (laser pulse) energy, the pulse duration must be shorter than the heat diffusion time, $\tau_{HD}$. A typical heat diffusion time for preferred nanoparticles with dimensions of 10-100 nm is in the range of nanoseconds. Therefore, an electromagnetic pulse of near-infrared radiation from a q-switched laser with a duration of a 3-10 ns may be an example of a preferred pulse duration.

Sometimes, however, for the sake of cost reduction, pulsed optical sources are being replaced with continuous wave sources (11,16). In case of significant contrast between tumor cells and normal cells, one of ordinary skill in the art can design a successful treatment procedure even using continuous wave (over 1 sec long pulses). Nevertherless, short pulses having duration equal or shorter than the time of thermal diffusion from the heat source to surrounding tissue, will result in much more effective thermomechanical interaction and much better spatial confinement of the damage effects (2-4).

Formula (eq. 3) is true until the temperature reaches 100° C. Then, any additional absorbed energy may contribute to the evaporation of the water around the particle, as well as heating the particle above 100° C. Employing $\Delta T=80°$ K., the difference between room temperature and boiling temperature of water in formula (eq. 1), minimal optical fluence required for generation of vapor bubble around absorbing nanoparticles can be calculated.

For example, assume the diameter of a spherical gold nanoparticle is d=200 nm. The heat diffusion time from this particle to water equals 12.8 ns. Then for a typical laser pulse of 12.8 ns in duration, formula (eq. 3) will yield F=0.6 mJ/cm$^2$, which is the critical fluence needed to heat up the spherical gold nanoparticles to 100° C. It can be predicted that any fluence larger than 0.6 mJ/cm$^2$, will result in superheating and possibly evaporation of water around the nanoparticle. Assuming that evaporation, at least in the stage of a thin nanobubble around nanoparticle, does not prevent the nanoparticle from being further heated, the optical fluence that corresponds to a temperature increase in a 200-nm diameter nanoparticle to 374° C. equals 2.6 mJ/cm$^2$. This is a temperature at which conversion of water into vapor occurs instantly.

Figure 3:
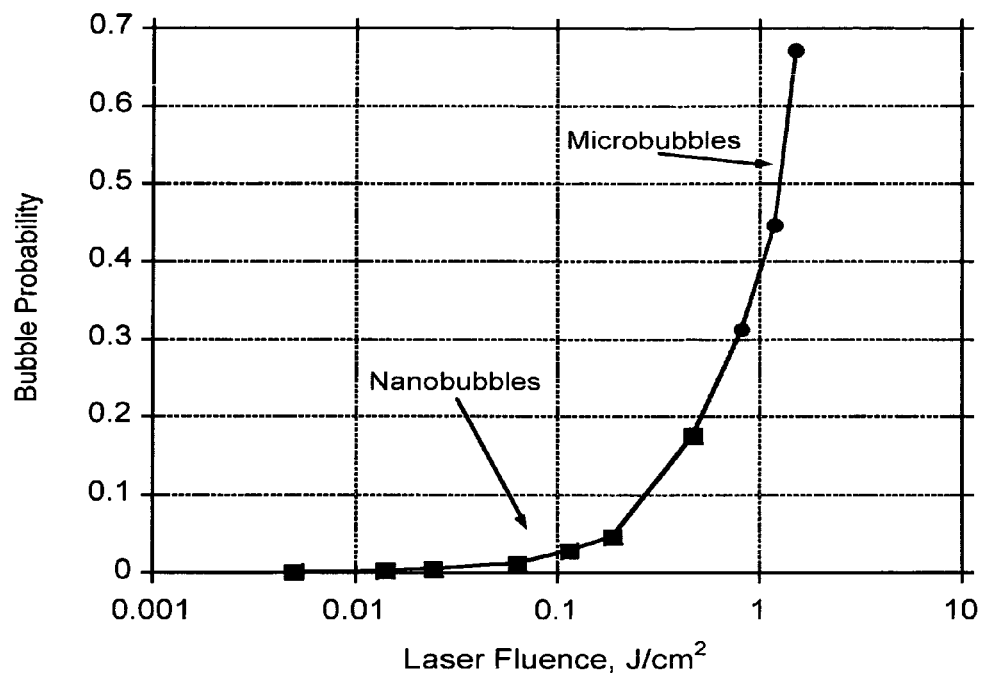
FIG. 3 shows optoacoustic signal as a function of laser fluence incident upon suspension of spherical gold nanoparticles with 100 nm diameter. Absorption cross-section of these nanoparticles, $\sigma_a=1.4\times10^{-9}$ cm$^2$. A sharp increase in the signal occurs at about 1 J/cm$^2$ indicating contribution of vapor bubbles to the optoacoustic signal. Note that the threshold of deviation of the optoacoustic signal from the linear curve of thermoelastic expansion occurs at a fluence much greater than the fluence, F=0.0026 J/cm$^2$, corresponding to the critical temperature of water, 374° C.

Surprisingly, however, no bubbles were detected at this level of fluence of laser irradiation. FIG. 3 depicts a magnitude of optoacoustic signal as a function of laser fluence. No deviation occurs at 2.6 mJ/cm$^2$ from a typical linear curve describing thermoelastic expansion of water. This means that at this level of optical fluence microbubbles do not occur. If any nanobubbles occur, they cannot contribute to the optoacoustic signal or to thermomechanical damage to surrounding the body.

Results presented in FIG. 3 and the calculations above show that the threshold of microbubble generation should decrease with increase of the size of nanoparticles. On the other hand, a very strong absorption of electromagnetic radiation due to plasmon resonance may be lost by a large nanoparticle, e.g., microparticle, since plasmon resonance theory requires that the size of the nanoparticles must be smaller than the electromagnetic wavelength. Furthermore, microparticles are not practical from the clinical prospective, since these particles are too large (heavy) to be suspended in water and can not propagate through biological cells and tissues, which makes targeting of these types of particles to a cell or other biological body difficult or impossible. Based on these considerations, clusters of nanoparticles can be used to effectively target cells and then to effectively generate vapor microbubbles by a low fluence laser radiation. If an ideal size cluster can be formed selectively in target cells, the laser fluence required for cell damage will be in the range of only a few mJ/cm$^2$, which is absolutely safe for normal cells and tissues.

Figure 4:
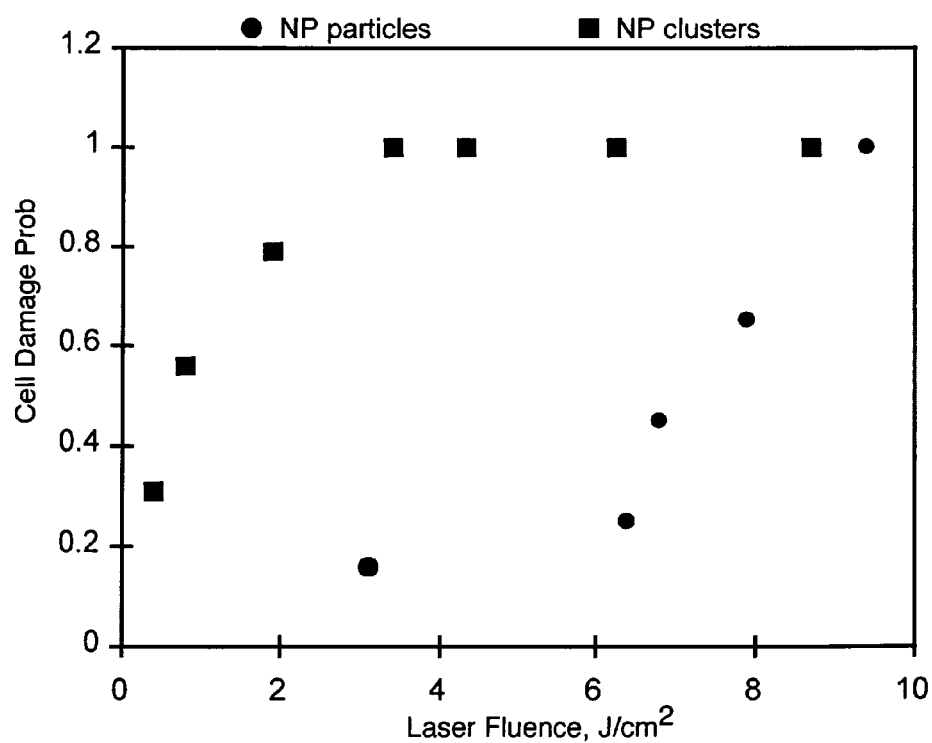
FIG. 4 shows threshold fluence for the laser damage of tumor cells targeted with gold nanoparticles that formed clusters inside the target cells.

FIG. 4 demonstrates the threshold of microbubble formation from laser irradiated clusters of gold nanoparticles. A targeting protocol is designed, which resulted in the accumulation of clusters of about ten 30-nm diameter nanoparticles in the target tumor cells, human B-lymphoblasts. The threshold fluence of the cell damage, confirmed with observation of the microbubbles by photothermal detection, was found to be about 100 mJ/cm$^2$, which is 50-60 times lower than that observed for individual gold nanoparticles with diameter 200 nm and 30 times lower than the cell damage threshold for cells nonspecifically targeted with the same 30-nm diameter nanoparticles. Both the microbubble generation threshold and the threshold of cell damage was always significantly higher in cases when no clusters in cells was observed.

FIGS. 1A-1B showing absorption coefficients of gold and silver nanorods and expressions (eq. 1), (eq. 2b) and (eq. 3) permit estimation of a nanoparticle temperature for a nano-ellipsoid of revolution. Assume a gold nanorod with diameter of 20-nm and length of 100-nm. Its absorption cross-section is 8.5×10$^{-10}$ cm$^2$, i.e. almost equal to that of a gold nanosphere with diameter of 200 nm, while its volume is only 200 times smaller than that of the nanosphere. Significantly stronger optical absorption of gold nanorods compared with gold nanospheres of equal volume results in a dramatically reduced minimum laser fluence required to heat up nanorods to a temperature required for vapor bubble formation. Thus, clusters of elongated metal nanoparticles are preferred over clusters of spherical metal nanoparticles for producing near-infrared radiation induced microbubbles. FIG. 2 shows that experimentally measured optical properties of actual gold nanorods are very close to those calculated theoretically.

Recent developments in nanotechnology allow for engineering nanoparticles with various shape and dimensions thereby facilitating the development of new imaging and therapeutic nanoparticulates. Colloidal gold is especially attractive since it is inert material that has been used for therapeutic applications (49-50). It is noteworthy to mention that upon intravenous injection of gold nanoparticles, unattached nanoparticles that could be a source of background noise for LANTCET can be rapidly removed from the circulating blood pool by liver and other organs of the reticuloendothelial system (51).

In summary total absorbed energy of electromagnetic radiation is proportional to the volume of a nanoparticulate. Thus, the total thermal energy stored in said nanoparticulate is also proportional to its volume. Heat diffusion rate decreases with nanoparticle dimension to the second power. Probability of microbubble generation is inversely proportional to dimension, i.e., surface tension, and viscosity that strongly affects the bubble generation is proportional to the nanoparticle dimension to the second power. These factors require that a nanoparticulate cluster is formed to reduce the threshold of microbubble formation, that can be used for LANTCET.

Real-Time Imaging and Monitoring

Lapotko et al (21-23) teach a method and apparatus for obtaining an image of a body, e.g. a cell, to allow examination of a number of submicron heterogeneities simultaneously, such as microbubbles or heated areas, including a method for detecting size. A relatively large sample surface, bigger than the cell diameter, is exposed to the pump laser radiation. The size of the surface exceeds the wavelength of the pump laser beam used. In fact, a surface of any size could be irradiated, but, logically, the size could not exceed the size of the sample itself because the chosen probe laser beam diameter is not smaller nor comparable with the pump laser beam diameter and is not larger than the maximum overall dimensions of the sample.

Spatial distribution of absorbing heterogeneities, e.g. bubbles, in the irradiation zone is determined by the synchronous measurement of the diffraction limited phase distribution through the whole cross-section of the probe laser beam which is transformed into an amplitude image by a phase contrast method. The size of separate microheterogeneities larger than the pump laser beam wavelength is determined by analyzing the amplitude image structure. The amplitude image corresponds to the refraction index change distribution induced by the pump laser in the object observed.

The average size of microheterogeneities smaller than the wavelength is measured indirectly by the characteristic time of cooling which is dependent on the size. That measurement is based on the speed measurement of the phase change of diffraction-limited images of those microheterogeneities at various points of the probe laser beam cross-section at different moments in time. Measurement begins right after pump laser irradiation has taken place as the chosen irradiation period is much shorter than the characteristic time of cooling of the microheterogeneity observed.

A short-time irradiation can be performed by two methods. The first method uses a single laser pulse. It is the duration of the pulse that determines the period of effect. A pulse-periodic mode, usually with a porosity greater than 1, also could provide this effect. The second method uses continuous laser pump radiation that is intensity-modulated with a relatively high modulation frequency ranged from a few kHz to hundreds of MHz. In this case duration of a single effect is determined by a modulation semi-period. This effect repeats with the frequency determined by the laser modulation frequency. Information about the time of cooling would be carried by the probe laser beam time phase related to the pump laser beam time phase.

A number of versions of the probe beam realization could be used. For example, a part of the pump laser beam could be used as a probe beam. Propagating the probe beam through an additional optical delay line regulates its delay time as related to the main beam. The chosen probe beam intensity should be considerably (at least 5-10 times) lower than the main beam intensity, so as to have minimal effect on the measurement results.

The phase distribution of the probe laser beam in the function of the pump laser wavelength should be measured, so as to obtain information about spectral properties of separate microheterogeneities simultaneously with their sizes. It is suggested that said measurement is to be accomplished by at least two time delays as related to the pump beam pulse at every pump laser wavelength. Dynamic change of the microheterogeneities or microbubbles, induced by the pump beam, is examined by changing at least two phase images, one of which is obtained immediately before the pump pulse operation and the other obtained simultaneously with the pulse operation or with a delay, with their subsequent subtraction. This is particularly important in case there are insignificant alterations of the image structure which are difficult to identify using only one image, as the measurement precision is low.

For the LANTCET method, an additional optical system of phase contrast is used as an optical transformation unit to transform phase distribution in the probe beam cross-section to an amplitude image. A registration unit is a high-speed multi-channel photodetector, for example CCD-matrix, in the pulse mode to register the amplitude image of the probe beam at various moments of time as related to the moment of the pump laser pulse operation. Another version of the registration unit is a number of one-channel photodetectors used to register time amplitude changes for one or several zones in the amplitude image of the probe beam. The probe beam falls simultaneously on all the detectors due to a semi-transparent system of mirrors placed in the way of probe beam behind the phase-contrast system. Another solution is a consecutive spatial shift of said detector using an additional switch unit.

For examination of the microheterogeneities considerably smaller than the wavelength, the fundamental solution is to introduce a synchronizing unit and a time delay regulating unit connected with each other, with the pump laser units, with the probe laser forming unit, and with the registration unit. A gradually regulated delay provides, when using a probe laser and pump laser pulse regimens, a precise measurement of the cooling time for the absorbing heterogeneities heated by the pump pulse to estimate the average size of the heterogeneities. If the continuous mode of the probe laser is used, a synchronizing unit that switches the probe beam phase monitoring at the moment of the pump laser pulse operation is used.

In the continuous mode of the pump laser with intensity modulation, the device contains an additional intensity-modulating unit placed in the path of the pump beam distribution. Registration of the continuous probe beam modulation caused by pump radiation, via refraction index modulation, is provided by the synchronous integrating unit connected to a photodetector or multi-channel photodetectors of the probe beam. The unit also receives a signal from the pump beam modulator. The necessary information about the pump laser (time) phase is carried by the signal.

Also provided is a one-channel mode, where pump radiation accomplishes the probe beam functions simultaneously. In this case phase distribution in the pump beam cross-section itself is registered. The filter cutting the pump beam in front of the photodetector should be removed to follow this scheme.

The system of splitting the pump laser beam into a main beam and an additional beam is introduced into the path of the pump beam, coming from the pump laser to use part of the pump laser as a probe beam, the additional beam accomplishing the probe beam function. The optical delay line connected with the time delay unit is introduced in the path of the probe beam.

A probe beam-forming unit can be realized both as a continuous laser connected with the synchronizing unit and as a pulse laser connected with a time delay unit. A probe beam turning unit should be introduced as related to the sample observed to obtain a three-dimensional tomographic image. Another version is to introduce the turning unit of the sample itself, where the turning unit is connected with the synchronizing unit. The device can also be equipped with an image processing unit connected with the photodetectors, the synchronizing unit, and the time delay unit. Its functions include image comparison at various moments of time, and another one is comparison of photothermal and regular optical images.

The device is additionally equipped with a pump beam wavelength-changing unit connected with the pump laser unit. Various methods can be used to provide the laser wavelength change. These methods include temperature and pressure influence on the active element; using spectral elements within a pump laser resonator in the form of a prism, diffraction grid, interference filters, or other applicable elements.

LANTCET begins when the object containing absorbing microheterogeneities is irradiated with a probe laser beam where the chosen probe beam diameter is not smaller than the pump beam diameter and is not larger than the maximum overall dimensions of the sample. Intensity of the probe beam should be considerably, i.e., at least 5-10 times, smaller than the pump beam intensity to cause minimal effect on the measurement results. The diffraction-limited distribution of the probe laser beam phase over the whole cross-section is then transformed to an amplitude image using the phase contrast method. The obtained values of the probe beam phase $\phi_0(x, y)$ and the phase-corresponding amplitude $I_0(x', y')$ of the image are basic for further analysis.

The next step is irradiation of the object containing absorbing microheterogeneities by a focused pump laser beam having a short pulse width and a wavelength coinciding with the absorption line of the microheterogeneities. The pump pulse immediately irradiates a relatively large sample surface, where the size of the surface is larger than the wavelength of the pump laser used. In fact, the surface could be of any size, but logically, it couldn't be larger than the sample itself. If such an effect occurs, light energy absorption in the sample is not uniform: microheterogeneities absorb light most actively. Thus, a live cell has various absorbing structures, e.g., cytochromes, organelles, and mitochondria, the size of which vary from a few nm to hundreds of nm, i.e., considerably smaller than the average size of a cell (5-20 microns). However, their ability to absorb light is so high, that it causes thermal effects causing a temperature rise 10-1000 times higher than the temperature of the cell's environment. Cooling of the structure that has absorbed light energy begins by heat diffusion after the end of the pump pulse operation.

The time of cooling for a single sphere-looking object is:

$$\tau_T = \frac{R^2}{6.75K}, \quad \text{(eq. 4)}$$

where
$t_T$ is the time of cooling of the object, sec;
R is the radius of the object, m; and
K is the temperature conductivity coefficient (m²/c).
This time equals $10^{-5}$-$10^{-4}$ sec for the majority of blood cells.

A primary thermal response could be presented as the distribution of temperatures over the x-axis and the y-axis:

$$\Delta T(x, y) = \alpha(x, y, \lambda)\frac{\varepsilon(x, y)}{\rho C}, \quad \text{(eq. 5)}$$

where
$\Delta T$ is the distribution of temperatures over the x- and y-axes,
$\alpha$ is the light energy absorption coefficient with the wavelength,
$\rho$ is density, kg/m,
$\epsilon$ is energy density in the pump beam, J/m²,
C is thermal capacity, J/kg ° C.

Expressions (eq. 4) and (eq. 5) help estimate the temperature effect both for an object (a cell) as a whole and for its structural elements, i.e., absorbing heterogeneities. The intensity of the effect depends on a specific absorption coefficient and the heterogeneity's size. $t_T$ would be about $10^{-8}$ s and less for the submicron structures having the sizes smaller than the wavelength ($10^{-7-8}$ m). It means that significant rise of the local temperature could be achieved only providing the pump pulse width or the modulation period T=1/f (where f is a modulation frequency) are smaller or at least comparable with $t_r$. Otherwise the local temperature effect, being the very source of the local heat variations of the refraction index, would not be achieved. The local heat variations of the refraction index $\Delta n(x, y)$ induced by the pump pulse absorption could be presented as follows:

$$\Delta n(x, y) = \alpha(x, y, \lambda)\frac{\varepsilon(x, y)}{\rho C}\left(\frac{dn}{dT}\right)p, \quad \text{(eq. 6)}$$

where
$\alpha$ is the light energy absorption coefficient with the wavelength,
$\rho$ is density, kg/m,
$\epsilon$ is energy density in the pump beam, J/m²,
C is thermal capacity, J/kg ° C.; and
T is temperature.

A further step comprises irradiating the object containing heated absorbing microheterogeneities by the probe laser beam where the chosen probe beam diameter is not smaller than the pump beam diameter and not larger than the maximum overall dimensions of the sample. Intensity of the probe beam should be considerably, i.e., at least 5-10 times, smaller than the pump beam intensity to cause minimal effect on the measurement results. The phase of the probe beam wave front will be distorted from the local heat variations of the refraction index when the probe beam would propagate through the sample. The phase deviations $\phi\Delta(x, y)$ could be described as follows:

$$\varphi\Delta(x, y) = L\alpha(x, y, \lambda)\frac{2\pi\varepsilon(x, y)}{\lambda_0 \rho C}\left(\frac{dn}{dT}\right)p, \quad \text{(eq. 7)}$$

where

L is the geometrical length of the probe beam way in a heterogeneity, n is the refraction index, Δn is the refraction index variations on the x- and y-axes, α is the light energy absorption coefficient with the wavelength, ρ is the density, kg/m, ε is the energy density in the pump beam, $J/m^2$, C is thermal capacity, J/kg ° C., and T is the temperature.

In a further step the diffraction limited phase distribution of the probe laser beam over the whole cross-section is transformed to an amplitude image using the phase contrast method. Taking into account the values $\phi_0(x,y)$ and $1_0(x',y')$ previously obtained in an unexcited state, parameters of the probe beam propagated through the exited sample at the moment of time $t_0$ could be presented as follows:

$$\phi(x,y)=\phi_0(x,y)+\Delta\phi(x,y) \quad (eq. 8),$$

where $\phi_0$ (x, y) is the probe beam phase in the absorbing zone of an unexcited object $\Delta\phi$(x, y) is alteration of the probe beam in the absorbing zone of an unexcited body, $$I(x',y')=I_0(x',y')+S(x',y') \quad (eq. 9),$$

Where $I_0$ (x', y') is the amplitude of the photothermal signal in an unexcited state, S (x', y') is the required photothermal signal being subject to registration and analysis.

The size of separate microheterogeneities larger than the pump laser wavelength is determined using structural analysis of the amplitude image measured immediately at the moment of the pump laser operation and corresponding to the refraction index change distribution induced by the pump laser in the object observed. To determine the average size of the microheterogeneities smaller than the wavelength, the phase alteration speed of the diffraction-limited images of said microheterogeneities in various points of the probe beam cross-section should be measured. Measuring begins immediately after the pump pulse effect has taken place. To achieve this, the probe beam irradiation and the phase distortion analysis of the object are performed a number of times, e.g., at two moments of time.

The theoretical limit of this method is conditioned by the terminal time of transformation of optical energy to thermal energy which is $10^{-13}$ seconds for condensed mediums. This time corresponds to 1 Å and could be achieved using femtosecond lasers. The photothermal signal amplitude S is proportional to the temperature change in the absorbing zone and decreases due to thermal conductivity.

U.S. Pat. No. 5,840,023 teaches the acquisition of optoacoustic images with contrast agents. In this method, a short pulse of irradiation is followed by detection of the induced pressure wave, which is then used for generation of an image. In the practice of the present invention, the pulses of electromagnetic radiation preferably have a duration of about 10 ns to about 1000 ns. When the tissue to be imaged is simulated by a solid slab tissue, the radiation fluence on the surface of the slab is about 10 $mJ/cm^2$. For other configurations of the test sample or for living human or non-human bodies, the surface fluence will vary, but will always be in the range of about 1 to about 100 $mJ/cm^2$, which generally is considered safe.

In addition both photothermal and optoacoustic imaging, either simultaneously or sequentially, can be utilized to monitor pulsed laser interactions with nanoparticulates and their clusters in the course of LANTCET procedure. The monitoring method may include photothermal imaging and microscopy, optical and optoacoustic detection of thermal field, thermal lens and bubbles generated around nanoparticulates. The imaging can occur during administration of the nanoparticulate, immediately after administration, or at some later time to allow for accumulation of the agent in the target cell or other body.

LANTCET System

Figure 5A:
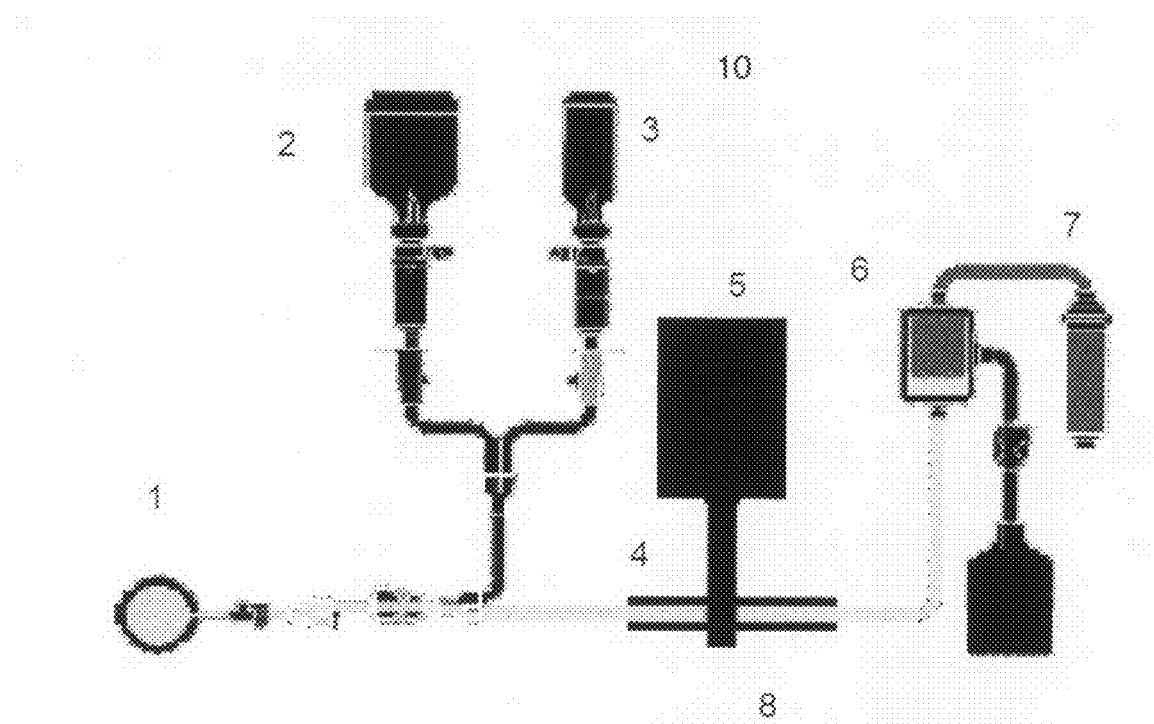
FIGS. 5A-5B show a sketch of a LANTCET system modified from a blood dialysis system (FIG. 5A) and a schematic diagram of LANTCET with simultaneous monitoring and guidance by photothermal microscopy (FIG. 5B).

FIG. 5A shows a designed system that utilizes the LANTCET method of laser activated nanothermolysis for purging tumor cells. For example such system may be a modification of a blood dialysis system where cells containing or accumulating bioconjugated nanoparticles can be irradiated extracorporally, i.e. outside human or animal body. The main components of the system 10 are the cell chamber 1, a source of targeting moieties 2, e.g., monoclonal antibodies or peptides, and nanoparticulates 3, an optical chamber 4, such as an optical flow cuvette, a pulsed source of electromagnetic radiation 5, and a means for filtering 6 and collecting 7 the products of damaging thermomechanical effects, e.g., a hemosorption system or similar system. The cell chamber 1 is independently fluidly connected to the source of targeting nanoparticulates 2,3, to the optical chamber 4 and to the filtering and collecting means 6,7. The pulsed source of electromagnetic radiation 5 is positioned to irradiate the cells in the optical chamber 4. Optionally, an imager 8 is positioned to receive a photothermal signal or for generating an optical image of thermomechanical effects affecting the cells in the optical chamber 4.

The system is configured so that bioconjugated nanoparticles can selectively target the cells in the cell chamber whereby nanoparticulate clusters accumulate in the cells. The targeted cells containing the nanoparticulate clusters flow to the optical cuvette where they are irradiated with laser or other electromagnetic pulses. The laser pulse heats the nanoparticulates which heat subsequently induces microbubble formation. The formation of microbubbles causes selective and increased levels of thermomechanical damage. Optionally, the imager may monitor the process of cell nanothermolysis by laser-induced microbubbles and/or direct the damaging thermomechanical effect against the targeted cells.

Figure 5B:
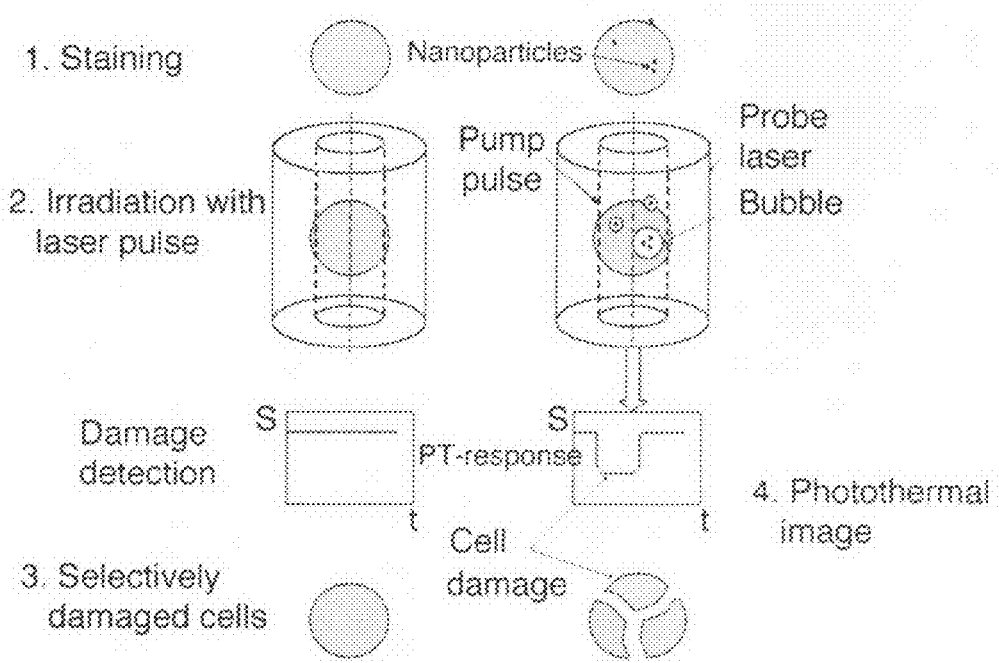

FIG. 5B depicts a schematic diagram of LANTCET with simultaneous monitoring and guidance by photothermal microscopy. In the diagram at (1) a mixture of cells is stained with MAB-conjugated gold nanoparticles that selectively attach to target receptors and form clusters (right); (2) cells are irradiated by a laser pulse that induces the bubbles around clusters of nanoparticles; (3) the bubbles destroy only cells targeted with nanoparticles and non-targeted cells (left) remain intact; and (4) a photothermal image shows tumor cells loaded with nanoparticles prior to pulsed laser irradiation and fragments of cells destroyed by the laser pulse.

The following examples are given for the purpose of illustrating various embodiments of the invention and are not meant to limit the present invention in any fashion.

Example 1

Laser Activated Nanothermolysis of Cultured Target Cells

Preparation of Cells

Several in vitro models were studied with myeloid cells of K562 cell line. These models used different protocols to couple nanoparticles to the cells. The test sample was prepared using selective targeting of leukemia cells with nanoparticle. Model leukemia cells at concentration of 800,000/ml in phosphate buffered solution (PBS) with 1% fetal bovine serum (FBS) were preincubated with two primary monoclonal antibodies CD15 and Glycophorin A (20 µl/ml of each) for 30 min with shaking in the dark at 4° C. After incubation the cells were centrifuged at 300 G for 4 minutes and washed twice. Then the cells were incubated again for 1 hour with $2*10^{10}$/ml of 30 nm gold nanoparticles conjugated to secondary monoclonal antibodies, goat anti-mouse IgG (TedPella Inc, Redding, Calif.). Then cells were separated from the nanoparticles by centrifugation at 300 g for 4 min. The bottom pellet of cells was resuspended in PBS-FBS solution and immediately used in laser experiments.

The same cells were used for preparation of 4 control samples where control #1 is the main control sample of cells was not pre-treated with primary monoclonal antibodies, but targeted with nanoparticles conjugated to secondary monoclonal antibodies, and control #2 is the secondary control K562 cells were nonspecifically targeted with gold nanoparticles using neither primary nor secondary monoclonal antibodies (nonspecific targeting), and intact control #3 the cells are without incubation, but with nanoparticles. Additional control #4 was prepared as a suspension of cell-free nanoparticles. To determine cell viability, trypan blue dye was used according to a routine protocol, on an aliquot of cells from the stock suspension before the laser treatment and on every treated sample after the laser treatment. The controls #s 1-3 were prepared for evaluation of efficacy of nanoparticle targeting.

Laser Treatment Procedure

LANTCET was experimentally studied in the two modes of laser irradiation. Both employ the method shown graphic depiction in FIGS. 6A-6B. In the first mode single cells were irradiated one by one and possible damage was detected immediately. After the incubation with gold nanoparticles, the samples of K-562 cells were immediately placed in a sample chamber (S-24737, Molecular Probes, OR) mounted on a microscopic slide to produce a monolayer of cells. Individual cells (total of 150) were irradiated within 7 min with 10-ns long single focused laser pulse at 532 nm with specific fluence. At this wavelength the light is strongly absorbed by nanoparticles, but not by the cells. All samples were exposed to the same laser irradiation conditions.

A photothermal (PT) microscope previously developed for visualization of vapor bubbles around laser-irradiated nanoparticles was used. PT microscopy may be used not only for detection of microbubbles around nanoparticles, but also for real-time monitoring of the laser-induced damage of individual intact cells with nano-second temporal resolution. Several quantitative parameters were measured: (i) probability of cell damage at a specific laser fluence as DP=M/N, where N is the total amount of irradiated cells, M is the number of cells that yield bubble-specific PT response; damage threshold fluence as the fluence corresponding to DP level of 0.5. Each individual (total of 150) cell was irradiated one by one with single focused laser pulse at 532 nm (10-ns duration) and the PT response from each cell was recorded with a photodetector measuring changes in the power of the probe laser at 633-nm (temporal profile of probe laser signal). Then DP was calculated for each cell sample.

The feasibility of LANTCET for purging was additionally evaluated using the second laser irradiation mode: a suspensions of test and control cells were injected into a flow rectangular glass cuvette and then were irradiated with laser pulses so that all cells in the cuvette were irradiated simultaneously (about 100 cells at a time). A broad laser beam (1 mm diameter) was scanned along the cuvette with dimensions of 0.4×0.1×10.0 mm. The procedure took about one minute for each sample. Then laser-induced cell damage was examined in 5 min in the same cuvettes by using an optical microscope and a digital camera. Additional evaluation of cell viability after the laser treatment was performed under an optical microscope following administration of the trypan blue dye into the cuvette and counting of positively-stained cells.

Electron Microscopy of Leukemia Cells

To visualize and count gold nanoparticle in K562 cells, the cell samples were examined with transmission electron microscope JEM 100 CX II (JEOL, Japan). Cell samples were fixed immediately after laser treatment. The amount of nanoparticle per cell was estimated by counting particles in EM images each visualizing a thin (60 nm) slice of a cell (total 30-40 cell images were processed for each sample), averaging counts in 4 microscopic slides and extrapolating obtained numbers to the total volume of the cell.

Figures 6A, 6B:
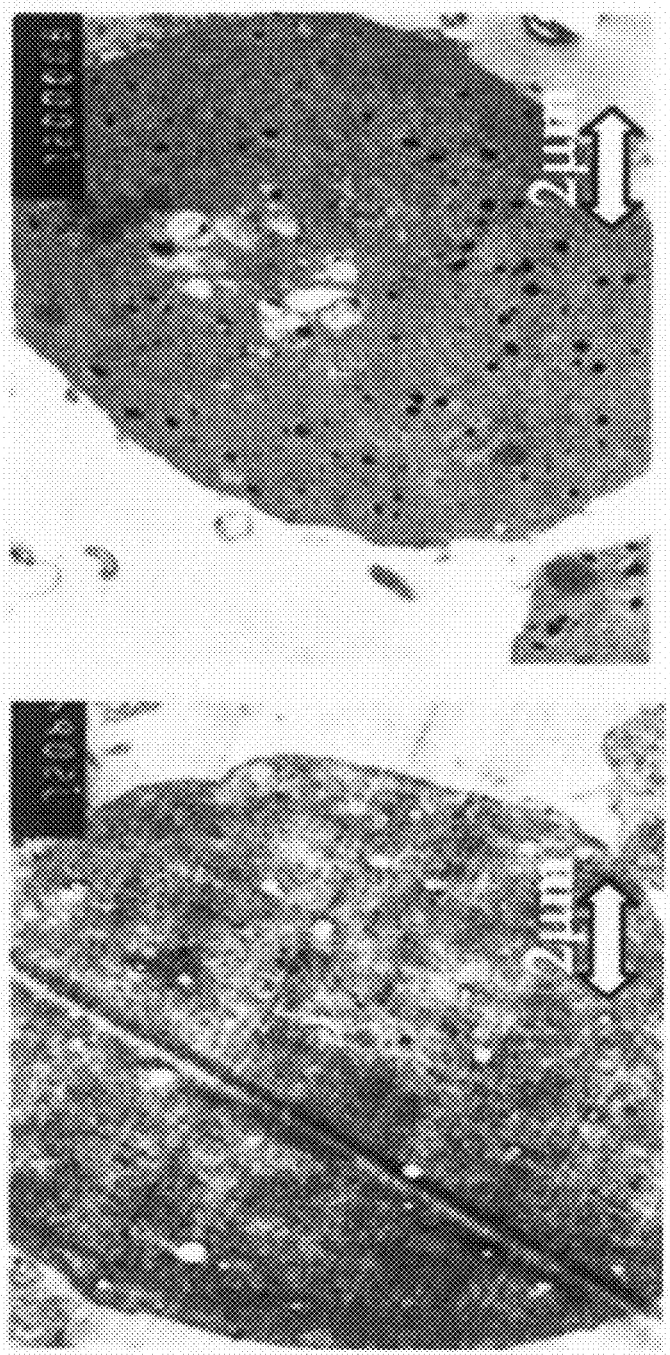
FIGS. 6A-6B show electron microscopy images of K562 cells control cell (FIG. 6A) without nanoparticles and a K562 cell selectively targeted with primary K562-specific antibodies and 30 nm diameter spherical gold nanoparticles conjugated to secondary monoclonal antibodies (FIG. 6B). Small black dots are single nanoparticles and larger black spots are clusters of nanoparticles.

Evaluation of Selectivity and Efficacy of Cell Targeting with Electron Microscopy Electron microscopy (EM) images of K-562 cells (FIGS. 6A-6B) revealed that nanoparticles fill the entire volume of the cell and do not concentrate only on its outer membrane where target receptors are located. Clusters of closely packed 5-10 particles were found in cells that were selectively targeted using the primary and secondary monoclonal antibodies (FIG. 6B). The total average number of nanoparticles per cell estimated by extrapolating the number of nanoparticles counted in 60-nm thin slices corresponding to EM images was about 31650 in selectively targeted cells. In contrast, a much smaller number of nanoparticles was found in controls, i.e., about 1500 nanoparticles per cell targeted with gold nanoparticle, but without primary monoclonal antibody, and about 200 nanoparticle per cell for direct targeting with unconjugated gold nanoparticle. No clusters were observed in any control sample (FIG. 6A). High nanoparticle contrast (ratio of test/control 1 was 21 and test/control 2 was 158) achieved by selective targeting of leukemia cells promises a high degree of LANTCET selectivity: only cells with clusters of nanoparticle may be destroyed while leaving other cells not damaged by laser pulse.

Cell Elimination Technology by Laser Ablation

Using the first irradiation mode, responses from individual cells to a laser pulse (532-nm, 10-ns) were studied. PT responses from the free space between the cells (background), from individual cells loaded with nanoparticles (test and controls) and from suspension of single nanoparticles without cells were obtained. Microbubble generation and cell damage were monitored simultaneously with a pump laser pulse by analyzing profiles and amplitudes of PT responses as depicted in FIG. 8. Among all studied samples, only the cells selectively targeted with gold nanoparticle showed prominent bubble-specific response (FIG. 7C). These cells also frequently exhibited apparent visual signs of the damage, i.e., fragmentation after irradiation with a single laser pulse.

Microbubbles with a duration 1-3.5 µs (FIG. 7C) were detected only among test cells, while in the controls such long microbubbles were never observed even at optical fluences 10 times exceeding the threshold of bubble generation. Long bubbles were detected only among those cells that manifested the clusters of nanoparticle in their EM images. Explanation for our observation can be found in previously discussed models of vapor bubbles generated around superheated nanoparticle. The temperature of laser-heated nanoparticle is proportional to the ratio $\tau_{HD}/\tau_L$ of heat diffusion time and the laser pulse duration, where the heat diffusion time from a spherical nanoparticle into aqueous medium can be found as the ratio of nanoparticle diameter squared and the heat diffusion coefficient ($\chi=0.0013$ cm$^2$/s) in water $\tau_{HD}=d^2/24\chi$. Heat diffusion time equals 0.3 ns for a single gold nanoparticle with diameter of 30-nm and this time is much less than laser pulse length (10 ns).

Such rapid heat diffusion redistributes thermal energy and prevents development of large microbubbles because only a 0.033 fraction of laser energy is used to heat the nanoparticle. The situation changes for a nanoparticle cluster with a diameter of about 200 nm consisting of about 5-20 nanoparticles. In this instance full thermal energy delivered with the laser pulse is utilized to heat a cluster volume, resulting in a much bigger vapor microbubble with maximal damaging power. Nanoparticle clusters were destroyed by single laser pulses with an optical fluence of J/cm$^2$, which could superheat nanoparticles to a temperature significantly above the evaporation threshold of gold (2,600° C.). Laser pulses, that followed the first microbubble-generating pulse, produced no bubbles and no bubble-specific PT response signals were detected for the second and the next pulses.

It is important to note the difference in PT response amplitude and lifetime (the latter corresponds to maximal bubble diameter) obtained from control sample # 4 (cell-free suspension of nanoparticle) (FIG. 7B) and from selectively targeted cells (FIG. 7C). Small-amplitude and short-duration (0.3 μs) PT responses were detected, indicating that only very short-lived nanobubbles were generated in the suspension of gold nanoparticle even with optical fluence 35 J/cm$^2$. To the contrary selectively-targeted with nanoparticle cells (test sample) produced much stronger PT responses (FIG. 7C) that indicates that bubbles were almost one order longer and therefore bigger in size. Such increase in bubble lifetime and size may be explained only by internalization of the clusters of nanoparticle into tumor cells.

Cell damage probability, DP, for test and control samples was analyzed at several different levels of laser fluence with main statistics acquired at 5, 35 and 70 J/cm$^2$ (FIG. 8). The DP level and laser fluence threshold for bubble generation depends on the presence of nanoparticle clusters in cells. The DP increases and damage threshold drops for test cells that may have clusters of nanoparticle compared to control samples for which no clusters were found during EM examination. For example, damage probability, DP, for selectively targeted cells reached its absolute maximum at a fluence of 5 J/cm$^2$, while for control #1 it was only 0.07 at the same fluence and for directly targeted cells (control #2) the DP was only 0.09 at much higher fluence of 35 J/cm$^2$. The damage threshold for the selectively targeted cells (test) is estimated to be about 1-3 J/cm$^2$ which is 30-100 times lower than fluence level for total destruction of the same cells without particles (control #3). Thus, selective targeting provided significant decrease of the laser damage threshold, that is, by almost 100 times compared to intact untargeted cells and by 30-50 times compared to directly targeted K562 cells. The length of PT response statistically varied from 0.2 μs to 3.5 μs. Maximal micro-bubble diameter reached 20 □m, as calculated using a previously developed model of cell damage and based on the experimentally measured bubble lifetime.

Figures 9A, 9B:
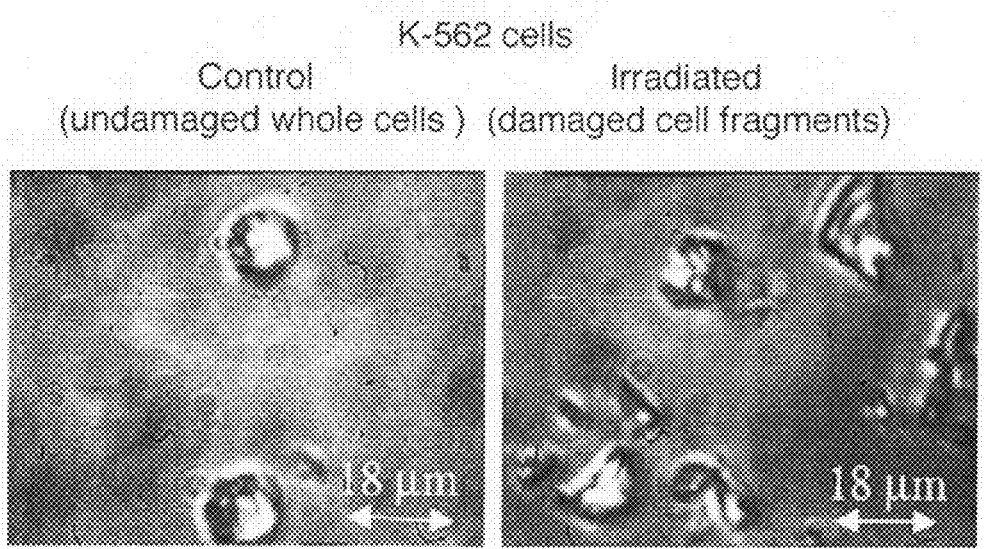
FIGS. 9A-9B are optical microscopic images of K-562 cells in 10 mm cuvette after irradiation with a single broad laser pulse with optical fluence of 5 J/cm$^2$.

In addition to laser irradiation of individual cells and their real-time monitoring with the PT microscope, whole suspensions of the same cells also were irradiated in the cuvette (second laser irradiation mode), simulating the first approximation to the purging procedure. In this case many cells (50-100) were irradiated simultaneously with a broad laser beam. The damaging effect of a single laser pulse was monitored by microscopic examination of cells in the cuvette after laser treatment. Cells with visual signs of destruction, as well as positively-stained (with trepan blue), were counted. Laser fluence of 5 J/cm$^2$ was used in this experiment. At this fluence, the controls (nonspecifically-targeted cells) were not damaged by single laser pulse (FIG. 9A). On the contrary almost all selectively-targeted cells were destroyed after a single pulse (FIG. 9B) as was verified by visual observation of fragmented target cells and by the trepan blue test.

Figure 7A:
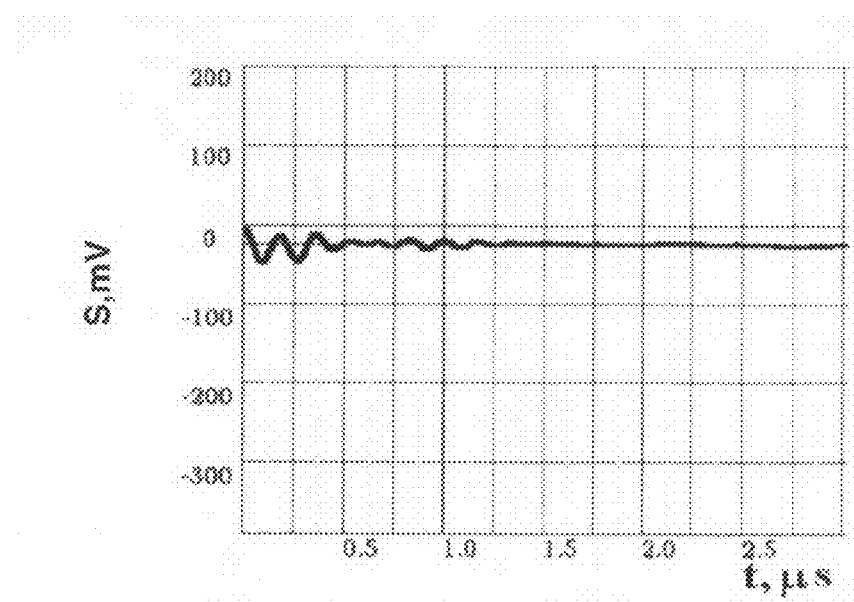
FIGS. 7A-7C show photothermal response signals obtained after irradiation with one laser pulse at 532-nm wavelength, and duration of 10-ns.
Figure 7B:
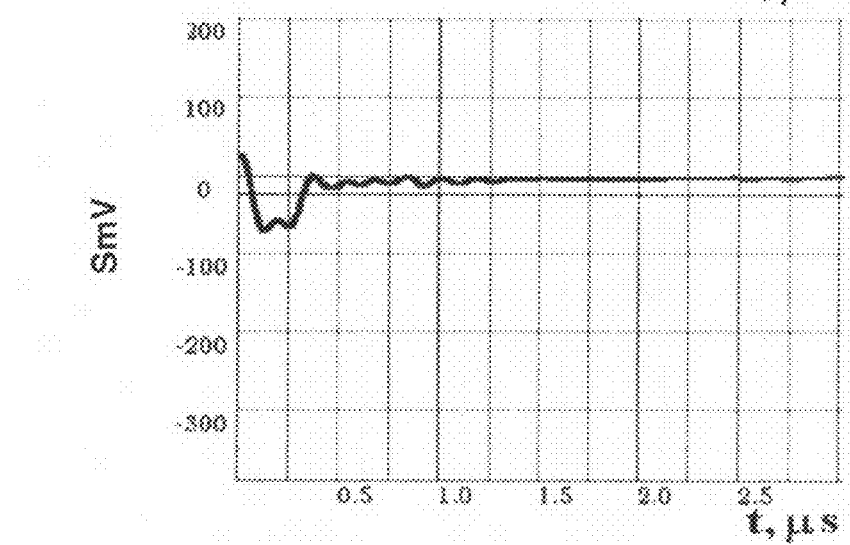
Figure 7C:
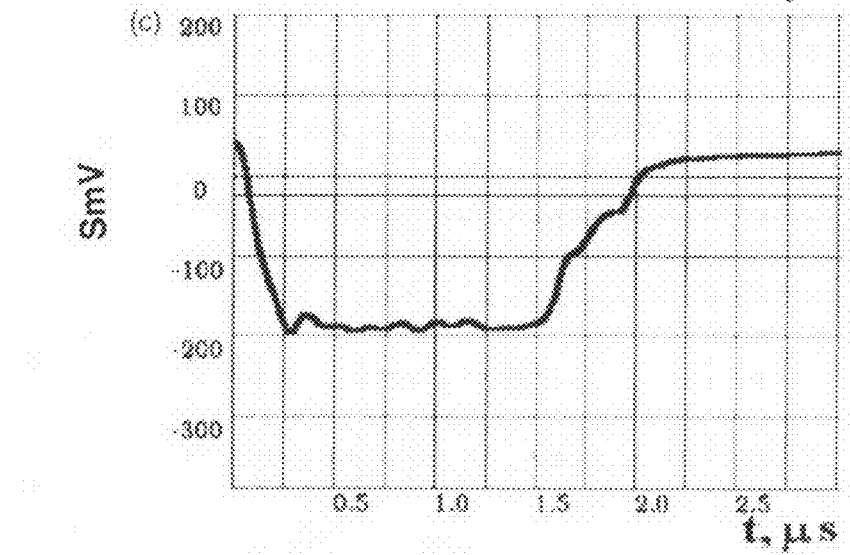
Figure 8:
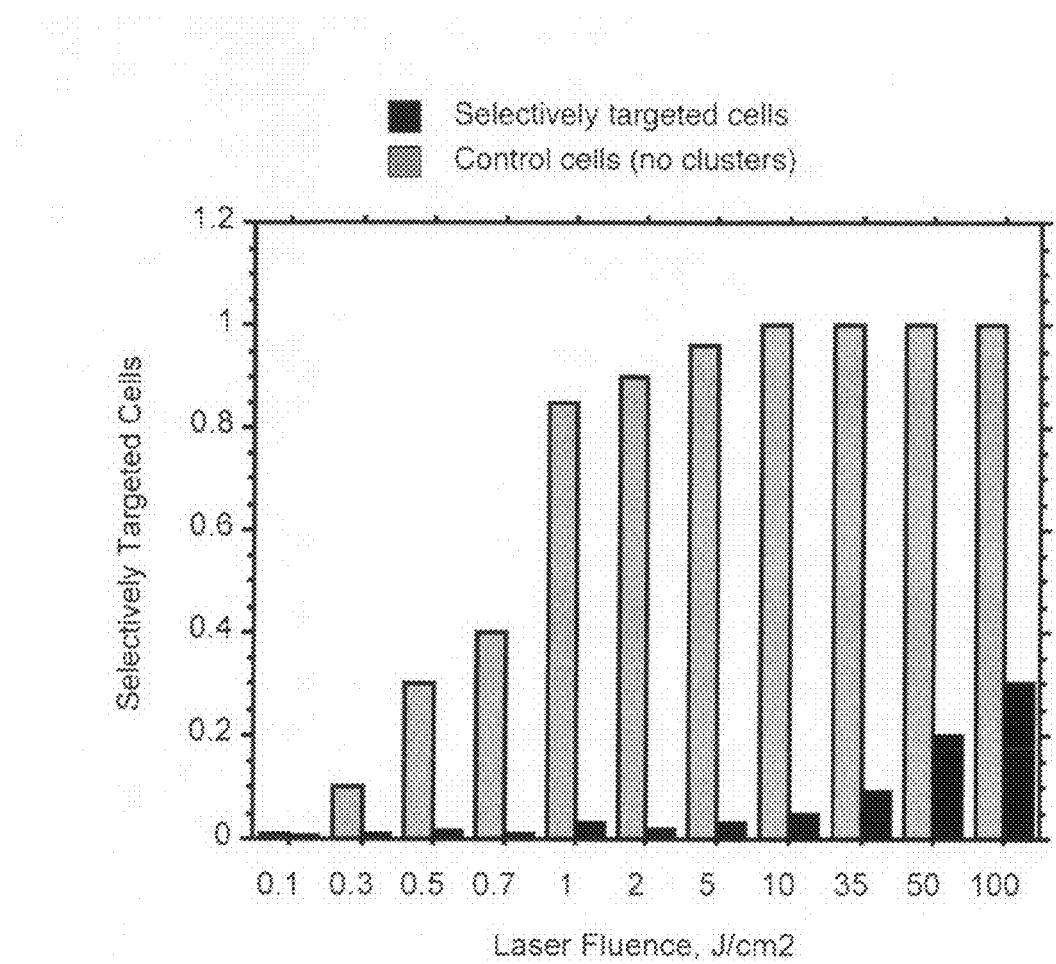
FIG. 8 shows the damage probability for K562 leukemia cells selectively targeted with gold bioconjugates that formed cluster of nanoparticles in the cells and the main control cells, incubated with nanoparticles conjugated with nonspecific mab.

The detected PT responses, as shown in FIGS. 7B-7C, are caused by the bubbles in cells and indicate cell damage/destruction. The latter also was confirmed with visual observation of cell disintegration (FIG. 9B) and also with positive staining of those cells with trypan blue. The laser-induced microbubbles and nanobubbles are the main damaging factor. Bubble generation may occur simultaneously at several points inside a cell volume. Laser-induced microbubbles with lifetimes of 0.5-10 μs may be comparable in size to cell diameter and mechanically damage the cell membrane thus causing necrosis, although smaller bubbles may also induce apoptosis without rupturing the membrane. Also microbubbles that emerge around free, i.e., out-of-cell, nanoparticles can not damage neighbor cells due to the limited diameter of such bubbles. The most surprising and important finding of this study is that formation of nanoparticle clusters caused microbubble formation around them and cell destruction even though the same laser pulses were safe for cells with single nanoparticles and for intact cells. Therefore LANTCET may provide highly selective elimination of cells.

Optimal bioconjugation and targeting conditions could enhance clusterization of nanoparticles on the surface and inside tumor cells, thus providing the necessary efficacy and safety of LANTCET as a purging method for treating peripheral blood stem cells transplants or grafts. There are several purging methods that also use metal (magnetic) particles and tumor-cell-specific monoclonal antibodies, e.g., magnetic sorting, drugs and photodynamic effects. None provides up to date sufficient efficacy in elimination of residual cells. It is contemplated that the combination of selective cell targeting with nanoparticles conjugated to specific monoclonal antibodies and methods of spectrally selective pulsed laser irradiation guided by photothermal microscopy may provide highly efficient purging of residual cells, and, thereby, improved efficacy and safety of autologous bone marrow transplantation.

It is contemplated that low fluence laser irradiation of cells with small concentration of single nanoparticles may cause apoptosis and delayed cell death. It also is contemplated that laser damage thresholds of such cells can be further reduced at least by several times after replacement of spherical gold nanoparticles with elongated gold nanoparticles (nanorods) or gold nanoshells possessing exceptionally strong optical absorption in the near-infrared spectral range. Simultaneously, laser irradiation in the near-infrared spectral range will be much safer for all types of normal cells. The efficacy and safety of LANTCET can be evaluated on leukemias in a clinic setting.

In conclusion, a new Laser Activated Nanothermolysis Cell Elimination Technology was experimentally demonstrated in vitro using model K562 cells treated with light-absorbing spherical gold nanoparticles and with laser pulses of specific wavelength and energy. Selectivity of suggested targeting schemes was directly verified by using electron microscopy. Selective targeting of K 562 cells resulted in their total destruction with a single laser pulse through generation of microbubbles inside the cells. Same cells with a lower level of nanoparticle and without nanoparticle clusters were not destroyed. It is contemplated that the LANTCET method may provide ultimate selectivity, safety and control for laser elimination of leukemia cells.

Example 2

Elimination of Human Leukemia Cells from Bone Marrow Transplant by LANTCET

The method for selective elimination of specific tumor cells includes the two main steps of cell targeting with nanoparticle and laser irradiation of cell mixture. The clusters of light-absorbing nanoparticles are sources of laser-activated microbubbles that are the main cell killing (eliminating) process. Selectivity of the formation of clusters of nanoparticles can be achieved by using a two-staged incubation procedure. At the first stage nanoparticles are selectively coupled to the membranes of specific cells. Monoclonal antibodies (MAB) that are specific primarily to membrane receptors, which are expressed mainly by target cells, are used. Those MABs are referred as primary MABs (MAB1) and they are first coupled to the receptors at cell membrane. Nanoparticles also are pre-conjugated with secondary MAB (MAB2), which have high coupling efficiency for MAB1. Then nanoparticle-MAB2 complexes are added and incubated with cell-MAB1 complexes so that finally the structures like cell-MAB1-MAB2-nanoparticle are created.

Unfortunately nanoparticles may also attach to membranes of non-specific cells. First, MAB1-specific receptors may be expressed in minor levels in some non-specific cells. Second, MAB2 may couple through different uncontrollable mechanisms directly to cell membranes regardless the cell type. As a result, a certain amount of nanoparticles will attach to membranes of non-specific cells, though their level will be much lower compared to that of specific cells (FIG. 10A). Therefore the selectivity of stage 1 is quite low and may cause unpredictable death among non-specific cells after exposure to laser radiation.

The second incubation stage may be used to improve the selectivity of the targeting. At this stage the temperature and time of incubation are set to stimulate formation of large clusters of nanoparticles in cells through internalization of the nanoparticles and their accumulation in endosomes. At the end of stage 2 the biggest clusters are formed only in the cells with a high initial level of membrane-bounded nanoparticles—in specific cells only (FIG. 10B). Due to a much lower level of nanoparticles in non-specific cells, the clusters either will not emerge inside them or will have a much smaller size. At the next step, a laser pulse of specific wavelength and matching the maximal light absorbance of the nanoparticles, energy and duration is applied to cell sample. The key idea of this step is that the threshold laser energy for inducing cell-damaging vapor bubbles depends on the size of bubble source—a cluster of nanoparticles. Laser energy (fluence) is set at the level that provides bubble generation only around the biggest clusters and does not induce any bubbles around smaller clusters or around single nanoparticles (FIG. 10C) because the threshold for bubble generation is inversely proportional to the diameter of the bubble source, if such diameter is less than 1 micrometer. This irradiation mode provides the selectivity of cell killing: no bubbles would emerge in non-specific cells even if the latter got some nanoparticles. Described procedures may improve the selectivity (safety) of LANTCET.

Cryopreserved samples of human bone marrow (BM): normal and diagnosed with acute lymphoblast leukemia (ALL) were used as suspensions of normal and tumor cells. Normal and tumor cells were prepared as separate samples and in an identical way by incubating them ex vivo with the same MAB1 and nanoparticle-MAB2 complexes. MAB1 type was determined by using standard flow cytometry protocol as diagnosis-specific MAB with the highest level of expression for each patient. For different patients the different MABs yielded the maximal expression level, but only one was used for each experiment: CD10, CD19, and CD20. A standard gold nanoparticle with diameter 30 nm and preconjugated with MAB2 (goat anti-mouse IgG(H+L)(AH)) were used as nanoparticle-MAB2 complexes (#15754, Ted Pella, Inc, Redding, Calif.). At the first stage nanoparticles were targeted to the cells at 4° C. This temperature prevents any internalization processes. At the second stage free nanoparticles were washed off and then the temperature was increased up to 37° C. to stimulate the internalization processes. The concentration of the cells then was adjusted to $2*10^6$/ml and laser treatment was applied. The samples were irradiated and studied in the sample chambers (S-24737, Molecular Probes, OR) on microscope slides.

Imaging and Measuring Nanoparticles in Individual Cells

CCD camera (model U2C-14S415, Ormins Ltd, Minsk, Belarus) with a 12-bit dynamic range and a sensor size of 1300×1000 pixels was used with a fluorescent light microscope (Leica D M L, Leica Microsystems, Wetzlar, Germany) with 100×-microobjective. Fluorescent signal amplitude was acquired and measured in counts (0-12 000) of camera digitizer. R-phycoerythrin (PE) fluorescent dye conjugated with anti-goat IgG (#P9787, Ted Pella, Inc, Redding, Calif.) was used as a marker for nanoparticles. Optimal concentration of PE was determined by flow cytometry.

For each cell optical and fluorescent images were obtained. Optical image was used for determining cell diameter and location of the outer membrane and nuclear membrane. Fluorescent images were analyzed with special software that was previously developed as a part of a photothermal microscope. Thus up to 40 parameters were obtained for each fluorescent image. Those parameters were used to analyze the mean level of nanoparticles in an individual cell, the level of nanoparticles in clusters, the spatial distribution of nanoparticles and their clusters inside the cell and the heterogeneity of spatial distribution of the nanoparticles. Conventional (non-confocal) microscopic image is the two-dimensional projection of three-dimensional distribution of fluorescent signals in the depth of focus of the objective. Nevertheless, membrane-type fluorescence can be differentiated from volume-type fluorescence and the uniform fluorescence can be differentiated from cluster-type fluorescence.

Photothermal Experiments

Photothermal experiments included laser irradiation of the cells and detection of laser-induced bubbles. The two experimental modes employed were single cell irradiation and PT analysis of laser-induced bubbles and suspension mode with simultaneous irradiation of many cells in suspension. In the first mode the photothermal (PT) microscope previously developed for visualization of vapor bubbles in cells was used. In this mode single cells were irradiated one by one after their positioning into the center of the laser beam and their PT signals were detected. Biological damage to irradiated cells was studied with the second mode through simultaneous irradiation of 4000-20000 cells. Suspensions of tumour and normal cells were analysed with a flow cytometer for actual viability levels and were injected into sample chamber that has a diameter of 2.5 mm and then were irradiated with broad laser pulses so that all cells were irradiated simultaneously. In this experiment, a broad pulsed laser beam (3 mm diameter, 532 nm, 10 ns) was used. Then the samples were collected from the chambers and were analysed to measure cell viability after laser treatment.

Cell Damage Detection

Laser-induced damage was measured by microscopy (concentration counts in hemocytometer) and flow cytometry (membrane damage detection) 2 hours after laser treatment. The former method detected the destruction of cells and the latter method detected necrotic death of those cells that were damaged, but not destroyed. Cells with compromised membranes that included propidium iodide (PI) were considered as damaged. The cells that were counted as PI-negative were considered as survived live cells. The level of survived live cells LLC was measured before and after laser treatment as a function of laser pulse fluence, number of laser pulses and incubation temperature during the second stage of cell incubation.

This parameter describes the relative change of the level of living cells in population due to laser treatment and counts cell losses due destruction and cell death:

$$LLC=(C_{al}/C_{bl}*C_{PI-}*100\%$$ (eq. 10)

where $C_{bl}$ is the initial concentration of all cells in the sample (counted in hemocytometer) before laser treatment, $C_{al}$ is the concentration of all cells in the sample after laser treatment (both counted in hemocytometer), $C_{PI-}$ is the level of PI-negative (live) cells obtained with flow cytometer (for MAB1-positive cells in the test and for all cells in the control) after laser treatment.

Accumulation of Nanoparticle in Cells

Figure 11E:
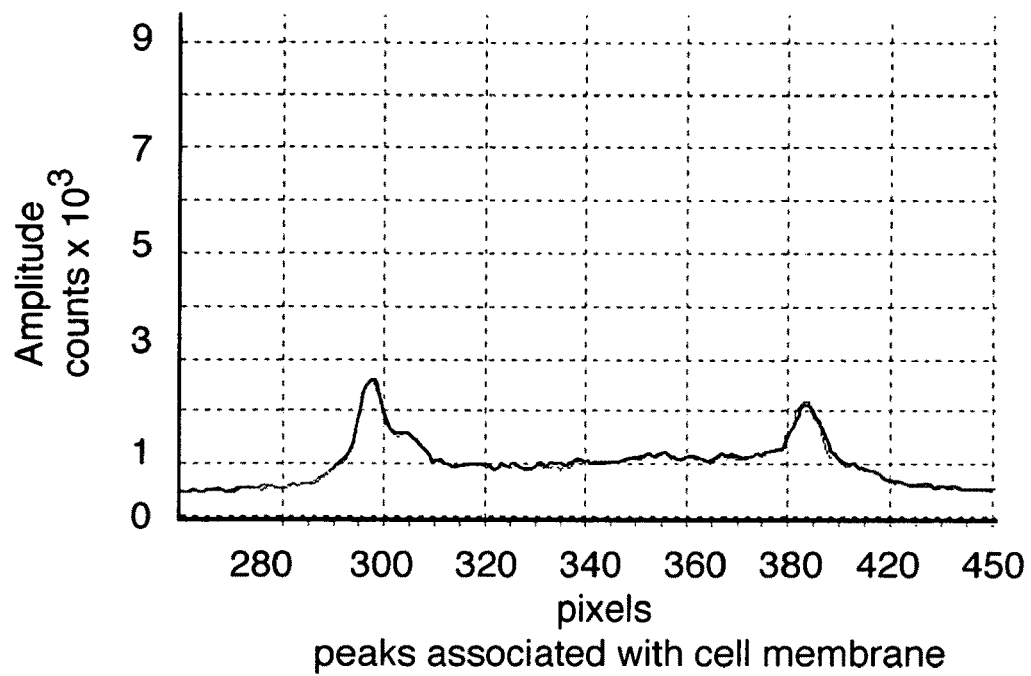
Figure 11F:
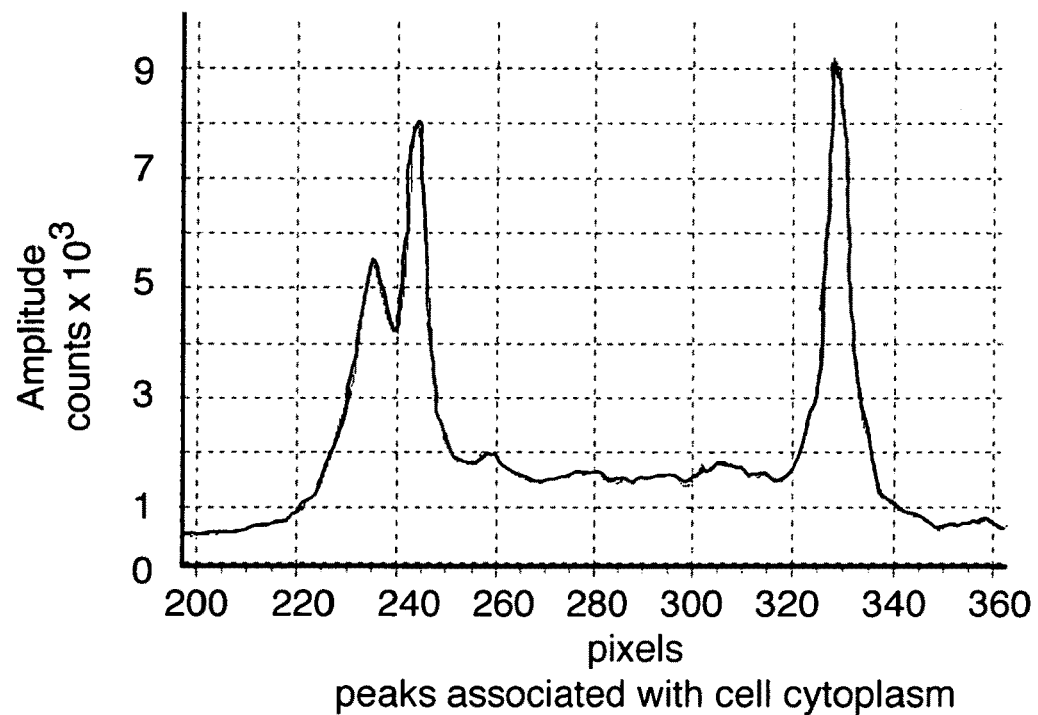

Fluorescent images of tumor cells showed the two types of signals: local peaks and uniform areas (FIGS. 11A-11F). Local and relatively strong fluorescent peaks were found in the most of the images of the tumor cells that were pre-incubated with nanoparticles. These peaks were associated either with cell membrane (FIG. 11C, 11E) or with cell cytoplasm (FIG. 11D, 11F). The amplitude in the peak (2000-10000 counts; FIGS. 11E-11F) was 5-20 times higher than that for cell areas with uniform signal (200-500 counts). All peak-related images had a similar shape, a round spot with the diameter 0.4-0.8 μm, that is close to the diffraction limit of the microscope. The signals of such shape and amplitude were never observed in cell-free space. Such peaks are considered as evidence for the clusters of nanoparticles.

Other fluorescent signals, i.e., large intracellular areas of a uniform low-amplitude fluorescence, may be caused by single non-clustered nanoparticles being uniformly distributed in the cell. The actual size of nanoparticle clusters could not be measured because it might be below the diffraction limit. Fluorescent images of normal bone marrow cells (not shown) that exhibited fluorescent signals and cluster-related peaks were similar to those obtained for the tumor cells (FIG. 11C). Although the total level of nanoparticle-positive normal bone marrow cells was within 6% for the same incubation conditions, the rest of the normal cells did not yield nanoparticle-specific fluorescence.

Figure 13A:
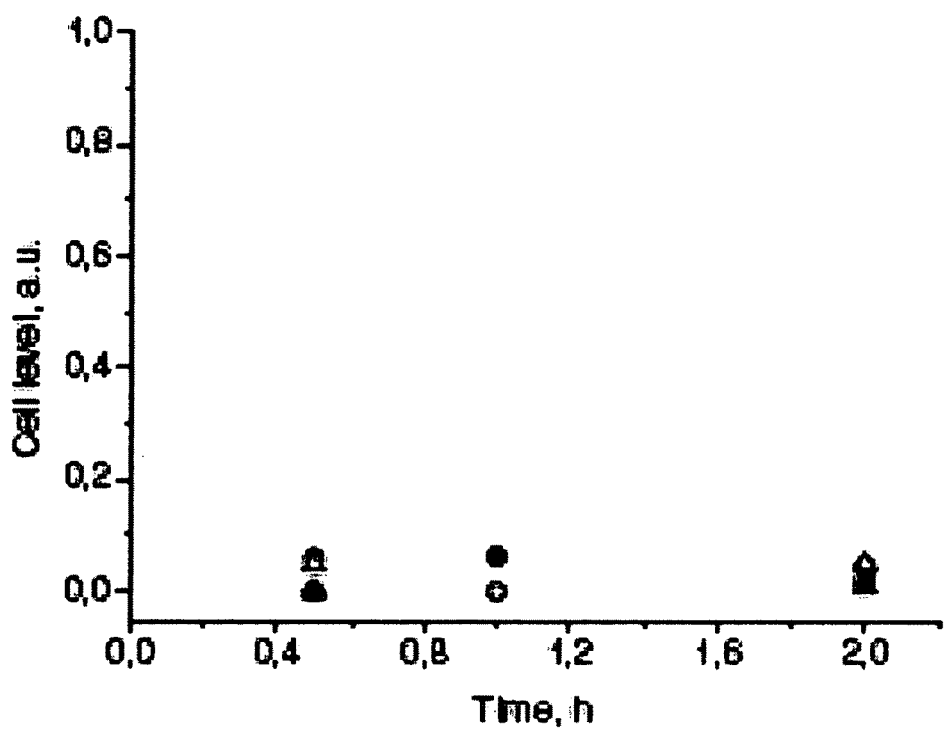
FIGS. 13A-13B show the kinetics of the clusterization of the nanoparticles during the second state of cell incubation at 4° C. and 37° C. in normal bone marrow cells (FIG. 13A) and in tumor cells (FIG. 13B) (○=37° C., peaks at membrane, ●=37° C., peaks inside cell; Δ −4° C., peaks at membrane, ▲ −4° C., peaks inside cell.
Figure 13B:
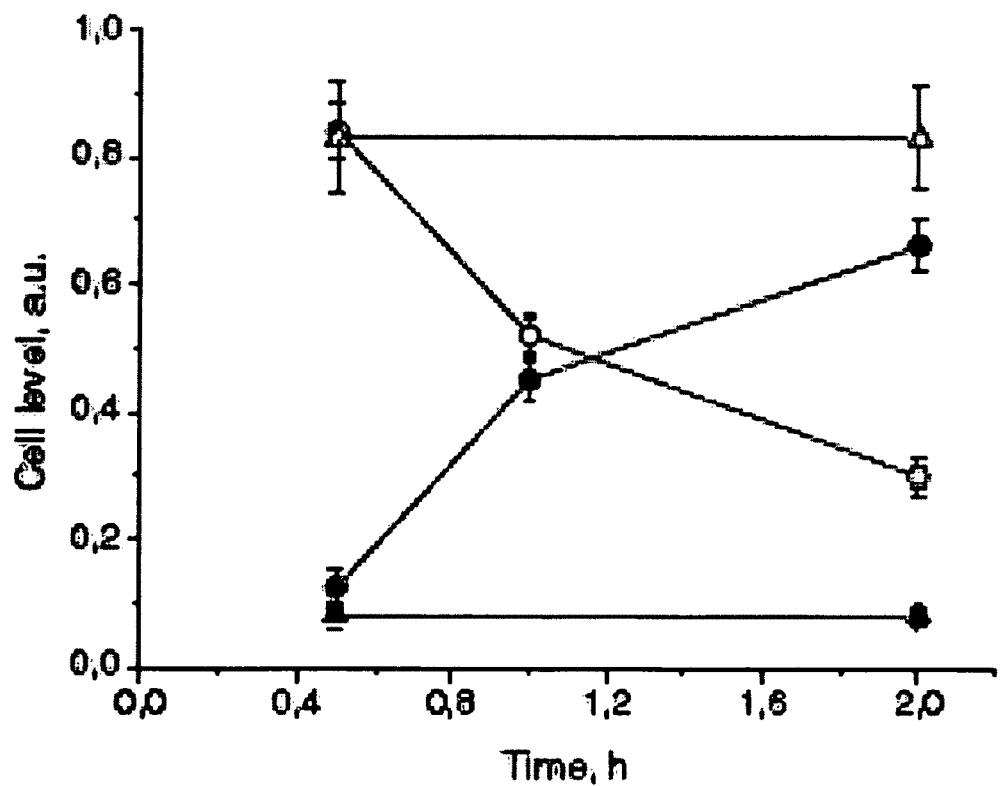

Influence of Time and Temperature During the Second Stage of Cell Incubation with Nanoparticle The peak amplitudes and homogeneous fluorescence in tumor and normal cells as function of the incubation time and temperature was measured during the second stage. All fluorescent images were analyzed in two ways. First, image parameters were calculated for each cell and were plotted as histograms for the different conditions of cell incubation (FIGS. 12A-12H). Second, cell counts were performed in three categories of fluorescent images: images without clusters; images with peripheral clusters only that are located at cell outer membrane; and images with peripheral and intracellular (located inside cell) clusters (FIGS. 13A-13B). Image parameters and cell counts were used to analyze the influence of incubation temperature and time, during the second stage of cell targeting, on the accumulation and internalization of nanoparticles in cells and on nanoparticle cluster size.

Distinct intracellular clusters of nanoparticle were discovered only for the tumor cells incubated at 37° C. (FIG. 11D, 11F) with fluorescent signals having maximal amplitudes of 8000-11000 counts. To compare the cluster size at various incubation conditions, the histograms were analyzed for the maximal values of fluorescent signal in peaks (FIGS. 12A-12D). This image parameter is important because the largest cluster of nanoparticles in the cell will produce the biggest bubble and thus such a cluster is the main killing nanostructure for the cell. Maximal peak amplitudes at 4° C. for incubated cells showed 2000-4000 counts, which is 2-4 times lower than that for 37° C. after 2 hours of incubation. This difference also may be interpreted as the difference in cluster size because the amplitude is proportional to the total number of nanoparticle in one cluster and the size of the cluster correlates to the number of nanoparticle in it. Therefore the incubation at 37° C. for 2 hrs provided the largest clusters of nanoparticle with their localization inside cells and in cellular cytoplasm.

Spatial distribution of fluorescent peaks was quantified through corresponding image parameter Mir and as function of the time and temperature of cell incubation (FIGS. 12E-12H). Histogram analysis of this image parameter showed a clear trend in re-localization of the clusters from the periphery (Mir value 0.6-0.8) to the inner site of the cell (Mir value 0.3-0.6) with the increase of the temperature and time of the second stage of incubation. It should be noted that observed internalization of nanoparticles was confined to the cytoplasm; the nanoparticle did not penetrate into cell nuclei which are quite large for this type of cells (FIGS. 11A-11D). Such spatial distribution of the fluorescent peaks can be explained by endocytotic mechanism of nanoparticle internalization.

Additional measurements were made to understand the kinetics of the internalization process. The cells were counted as the number of cells with intracellular peaks in their images and as the number of cells with membrane-located peaks in their images as function of cell incubation time and temperature at second stage of their targeting with nanoparticle (FIGS. 13A-13B). No changes were found in those categories for normal bone marrow cells (FIG. 13A) regardless of the time and the temperature of cell incubation. The counts of cluster-related cells were within 6% for any incubation conditions. For tumor cells the situation was completely different (FIG. 13B). Incubation at 37° C. caused a steady increase of the number of cells with intra-cellular clusters from 12% at the beginning of second stage to 66% after 2 hours. Under the same conditions (37° C.) tumor cells yielded a decrease in cell counts for membrane-located clusters from 84% at the beginning to 30% after 2 hours. Tumor cells that were incubated at 4° C. showed no changes at all in the counts of membrane-located and intracellular clusters (FIG. 13B).

Obtained experimental results demonstrated the formation of clusters of nanoparticle at cellular membrane and inside the cells and that the largest nanoparticle clusters internalize to the cytoplasm of tumor cell only during the second stage of incubation. The difference in nanoparticle levels in normal and tumor cells also prove high selectivity of the applied targeting method.

Laser-Activated Bubbles in Cells

Figure 14A:
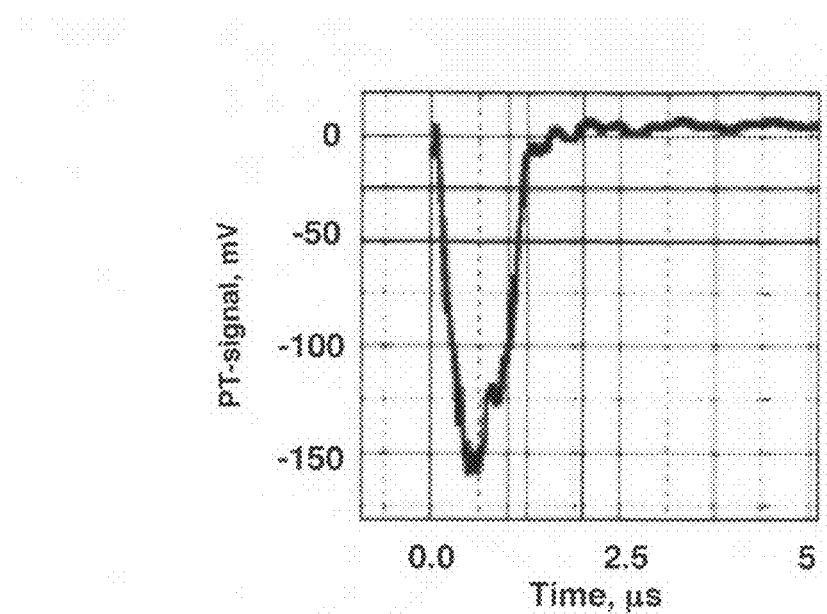
FIGS. 14A-14C show a typical bubble-specific photothermal response (FIG. 14A), a photothermal image (FIG. 14B) and an optical image of the same cell before irradiation (FIG. 14C) obtained for a tumor cell after single laser pulse for the incubation conditions being 37° C., 2 h.
Figure 14B:
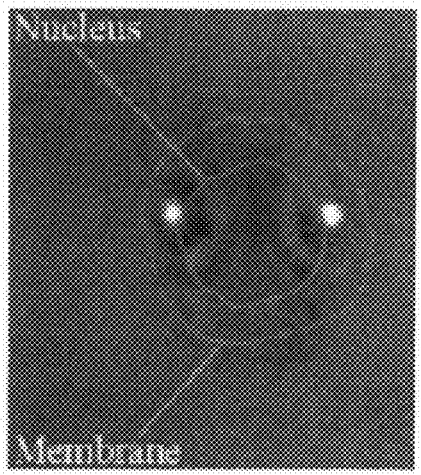
Figure 14C:
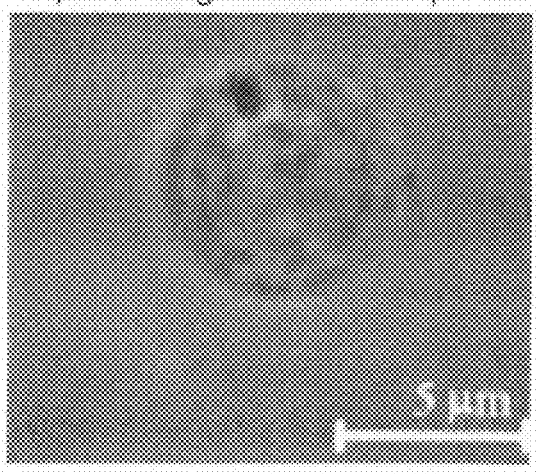

Photothermal (PT) responses and images were obtained for individual tumor cells at different laser fluencies. Typical bubble-specific PT responses and images that were obtained after a single laser pulse at 0.6 J/cm$^2$, 532 nm for incubation conditions of 37° C., 2 hrs are shown in FIGS. 14A-14C. The duration of the PT response allows measurement of the bubble lifetime and hence its maximal diameter can be estimated. Location of the bubble-specific signals in the PT image of the tumor cell (FIG. 14A) shows that the bubbles were generated in the cytoplasm and probably not in the area of the nucleus. The bubble generation sites spatially coincide with location of nanoparticle clusters as shown in the fluorescent images. Also it was found that the number of bubble-related signals in one cell, from 1 to 4, was lower than the number of cluster-related peaks, 4-20, in those cells. Therefore, under a given laser fluence of 0.6 J/cm$^2$, not every cluster produced the bubbles. It is likely that only biggest clusters of nanoparticles are cell damaging agents while the rest of smaller clusters and single nanoparticle may not produce the bubbles and therefore do not contribute into cell damage process.

The response of the bubble (FIG. 14A) was obtained at the fluence of 0.6 J/cm$^2$. No bubble-specific response was detected at the same fluence when water suspension of individual nanoparticles at a concentration of $8*10^{11}$/ml was irradiated. Also, such PT responses were not detected for normal bone marrow cells. This result may be considered as additional evidence that only the largest clusters of nanoparticles produced the bubbles at this fluence level. It also was discovered that the cells with nanoparticle clusters, shown in their fluorescent images, may generate repeatable bubbles during exposure to several of up to 60 laser pulses. Thus, the cluster of nanoparticles are a photostable structure, unlike the single nanoparticles that are destroyed after the first pulse, and can be irradiated with more than one laser pulse. Using the model of a laser-activated bubble, maximal bubble diameter is estimated as 13 μm for the PT signal (FIG. 14A). Such a bubble size is comparable with the cell diameter, that is, 8-9 μm (FIGS. 11A-11B) and therefore may rupture the cell membrane.

Laser-Induced Damage to Cells

Cell samples were irradiated in the round 2.5 mm cuvettes with single or several laser pulses at 532 nm. Cell damage was analyzed through LLC dependence upon laser parameters (pulse fluence and number of pulses) and incubation parameters (nanoparticle concentration, incubation temperature and MAB1 types). Influence of the laser parameters on the cell damage was studied for the same incubation conditions such as: one type of MAB1 (specific for each patient), incubation temperature of 4° C. and a nanoparticle concentration during the first stage of incubation of 15000 nanoparticle/cell.

Increase of laser fluence from 0.2 to 2 J/cm$^2$ caused a gradual decrease of LLC for tumor cells from 3.9% at 0.2 J/cm$^2$ to less than 1% at the fluencies above 0.6 J/cm$^2$. The samples obtained from 3 different patients with an ALL diagnosis showed different degrees of damage of tumor cells. At the fluence of 0.6 J/cm$^2$ and single-pulse irradiation, the LLC was found to be less than 0.1%, 1.5%, 5% respectively. These samples were treated with different MAB1 and the difference detected in LLC values may be caused by the variations in nanoparticle targeting efficacy. The change in LLC of the tumor cells after laser treatment was due mainly to the decrease in the concentration of cells, i.e., up to 10 times in comparison with initial concentration, and, to a lesser extent, to cell membrane damage. The LLC for normal bone marrow cells under the same conditions was found to be 77-84%. Irradiation of tumor cells with 10 laser pulses instead of 1 did not produce a significant effect; the LLC decreased from 1.5% to 1.2%. This means that the first laser-induced bubbles produce the damage and unlike the damage through heating the bubble-related damage does not have accumulative nature and occurs immediately after expansion of the first bubble.

Figure 15:
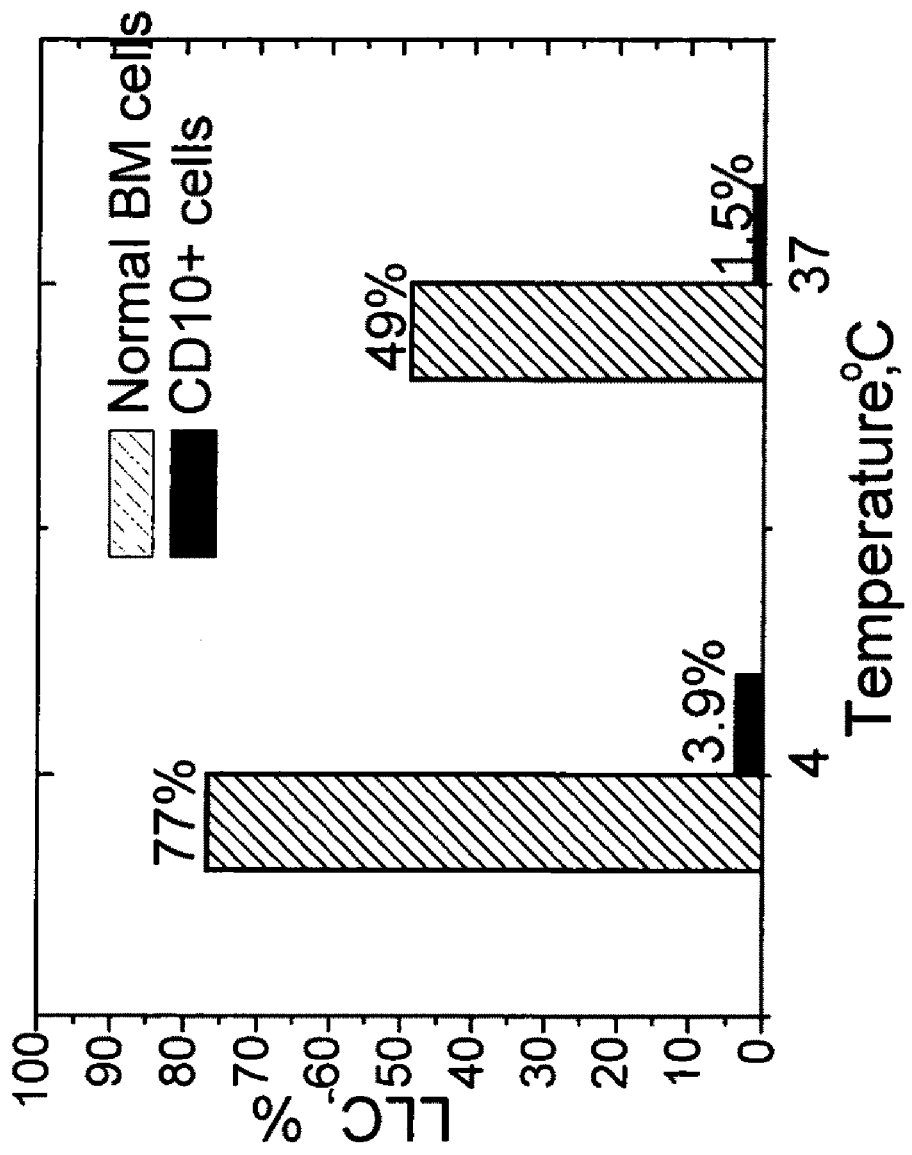
FIG. 15 shows the level of surviving live tumor cells LLC experimentally obtained after a single laser pulse (532 nm, 0.6 J/cm2) for the different primary MABs being applied during the first state of cell targeting NPS at 4 deg C. and 37 deg C.

The influence of incubation parameters on cell damage was studied. Under a fixed concentration of nanoparticles during the first stage of incubation, the application of the different primary MABs resulted in a variation of LLC from 0 to 67%. The strongest effect, that is when LLC is 0, was reached by using the combination of several primary monoclonal antibodies. The influence of another incubation parameter, the temperature of the second stage of incubation, is shown in FIG. 15. Increase of the incubation temperature from 4° C. to 37° C. caused a 2.6× decrease of LLC for tumor cells from 3.9% at 4° C. to 1.5% at 37° C. and a 1.6× decrease of LLC for normal cells from 77% at 4° C. to 49% at 37° C.). Therefore in terms of the efficacy of cell killing the two-stage incubation at 37° C. has produced better results than the standard incubation scheme at 4° C. Although "hot" incubation was less safe for normal BM cells. No significant variation of LLC for tumor cells was discovered when the concentration of nanoparticles varied from 6000 to 150000 nanoparticles/cell during the first stage of incubation. The LLC of tumor cells decreased from 15% (6000 nanoparticle/cell) to 10% (150 000 nanoparticle/cell). It is assumed that the concentration from 15000 to 30000 nanoparticles/cell is quite saturating, because further increase of nanoparticle concentration had no effect on cell killing efficacy.

In summary, it is demonstrated that clusters of nanoparticles with the maximal diameter and consisting of the maximal number of nanoparticles can be formed controllably by using the two-stage targeting, i.e., incubation. The described two-stage mechanism of nanoparticle targeting is universal and can be applied to different types of cells in addition to tumor cells. Two-stage targeting can be regulated through the control of the cell incubation parameters time and temperature at each stage. Also, the bigger internalized cytoplasmic clusters may generate laser-induced bubbles at the lowest fluencies of the laser pulse.

The following references are cited herein.
1. Welch, A. J. and Van Gemert, M. J. C. Optical-Thermal response of laser-irradiated tissue, New York, Plenum Press, 1995.
2. Vogel, A. and Venugopalan, V. Chem Rev, 103:577-644 (2003).
3. Anderson, R. and Parrish, J. Science, 220:524-527 (1983).
4. Oraevsky et al. J. Applied Phys. 78(2):1281-1290 (1995).
5. Oraevsky et al. IEEE J. S. T. Quant. Electron, 2(4):801-809 (1996).
6. Chen et al. Cancer Lett. 115(1):25-30 (1997).
7. Hasan et al. Photodynamic Therapy of Cancer, Holland-Frei Cancer Medicine, 6th Ed., Ch. 40, B. C. Dekker Press, 2003.
8. Nelson et al. Lasers Surg Med. 19(2):224-229 (1996).
9. Brinkmann et al. Lasers Surg Med. 27(5):451-64 (2000).
10. Jay, D. G. Proc. Natl. Acad. Sci. USA, 85:5454-5458 (1988).
11. Loo et al. Tech. Cancer Res. Treatment, 3(1):33-40 (2004).
12. Guzatov et al. Quantum Electronics, 33(9):817-822 (2003).
13. Copland et al. Molecular Imaging and Biology, 6(5):341-349 (2004).
14. Pitsillides et al. Biophys. J. 84:4023-4032 (2003).
15. O'Neal et al. Cancer Lett. 209:171-176 (2004).
16. Sokolov et al. Cancer Res. 63:1999-2004 (2003).
17. Oraevsky et al. Proc. SPIE, 4256:179-187 (2001).

18. Oraevsky et al. Proc. SPIE 2, 4434:60-69 (2001).
19. P. Carter, P. Nature Rev. Cancer, 1:118-129 (2001).
20. Koivunen et al. Nucl Med. 40(5):883-888 (1999).
21. Lapotko and Kuchinsky, Photothermal Microscope, in: F. Scudiery, M. Bertolotti, (Eds.) Photoacoustic and Photothermal Phenomena, AIP, Rome, 1998, pp. 184-186.
22. Lapotko, et al. Laser Surg. Med. 33:320-329 (2003).
23. Lapotko, D. and Romanovskaya, T. Proc. SPIE 3914:262-269 (2000).
24. Pui et al. New Engl. J. Med. 350(15):1535-1548 (2004).
25. Bazarbachi et al. LANTCET Oncol. 5(11):664-672 (2004).
26. Schrappe et al. Best Practise & Research Clinical Haematology, 15:729-740 (2003).
27. Faderl, S. and Estrov, Z. ALL Crit. Rev in Oncology/Hematology, 28:31-55 (1998).
28. De Lima, M. J. and Shpall, E. J. Current Hematol. Reports, 3:257-264 (2004).
29. Burt et al. Langmuir, 20(26):11778-83 (2004).
30. Farokhzad et al. Cancer Res. 64(21): 668-72 (2004).
31. Eghtedari et al. Proc. SPIE, 4960:76-85 (2003).
32. Beesley, J. E. Colloidal Gold: A New Perspective for Cytochemical Marking, Oxford, New York, 1989.
33. Hayat, M. A. Colloidal Gold: Principles, Methods, and Applications Vol. 3, Academic Press, New York, 1985.
34. Gregoriadis, G. and McCormack, B. Plenum, pp. 264-267 (1998).
35. Harris, J. (ed) Poly(ethylene glycol) chemistry, biotechnical and biomedical applications. Plenum Press, 35 New York, 1992.
36. Storhoff et al. J. Am. Chem. Soc. 122:4640 (2000).
37. Dujardin et al. Chem. Commun. 1264-1265 (2001).
38. Goodrich et al. Langmuir, 20(23):10246-51 (2004).
39. Guzatov, et al. Quantum Electronics, 33(9):817-822 (2003).
40. Yamada, et al. Chem. Commun. 23:2476-2477 (2001).
41. Vrouenraets, et al. Cancer Res. 61:1970-1975 (2001).
42. Ross, J. S. and Gray, G. S, Clin Leadersh Manag Rev, 2003; 17(6): 333-340.
43. Kong et al. Cancer Res. 61(7):3027-32.
44. Hainfeld, J. F. Scanning Electron Microscopy, 239, 254 (1995).
45. West, J. L. and Halas, N. J. Annu Rev Biomed Eng, 5:285-292 (2003).
46. Shih et al. Electrochemcial synthesis and optical properties of gold nanorods. In: Feldheim, D. M.; Foss, C. A. Metal nanoparticles: synthesis, characterization, and applications. Dekker, 2001:163-182.
47. Ahmadi et al. Science, 272: 1924-1926 (1996).
48. McKenzie, A. L. Phys Med. Biol. 35:1175-209 (1990).
49. Gumpel, J. M. Rheumatol Rehabil, 13:1-9 (1974).
50. Abrams, M. J. and Murrer, B. A. Science, 261:725-730, (1993).
51. McEntee, M. F. and Ficken, M. D. Avian Dis. 1990; 34(2): 393-397.
52. Safarik, I. and Safarikova, M. Cells isolation: magnetic techniques, in: Wilson, et al., (Eds.) Encyclopedia of Separation Science, Academic Press, London, 2000 pp. 2260-2267.

Any publications or patents mentioned in this specification are indicative of the levels of those skilled in the art to which the invention pertains. Further, these publications are incorporated by reference herein to the same extent as if each individual publication was specifically and individually incorporated by reference.

One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

What is claimed is:

1. A system for increasing selective therapeutic thermomechanical damage to cancer cells, comprising:
a chamber containing the cancer cells in a medium;
a source of nanoparticulates each comprising at least one antibody that specifically targets the cancer cells, said source of nanoparticulates fluidly connected to the cell chamber;
an optical chamber adapted to contain the targeted cancer cells fluidly connected to the cell chamber;
a pulsed source of electromagnetic radiation directed against the targeted cancer cells in the optical chamber, said source configured to emit a spectrum of wavelengths selected to have a peak wavelength that is near to or that matches a peak absorption wavelength of said nanoparticulates; and
means for filtering out cells damaged by thermomechanical effects resulting from absorption of the electromagnetic radiation emitted at the peak wavelength, said filtering means fluidly connected to the cell chamber.

2. The system of claim 1, further comprising:
means for receiving a photothermal signal or for generating an optical image of the thermomechanical effects.

3. The system of claim 1 wherein said at least one antibody is a monoclonal antibody.

4. The system of claim 1, wherein said nanoparticulate further comprises a surfactant or complementary strands of a nucleic acid conjugated thereto or a combination thereof.

5. The system of claim 1, wherein said nanoparticulate has a dimension of about 1 nm to about 1000 nm.

6. The system of claim 1, wherein said nanoparticulates are adapted to form one or more nanoparticulate clusters.

7. The system of claim 6, wherein said nanoparticulate cluster has a total volume about 2 to about 200 times greater than a volume of the nanoparticulate.

8. The system of claim 1, wherein said nanoparticulate is formed from at least partially metallic nanoparticles, nanorods or nanoshells or is a carbon nanotube.

9. The system of claim 8, wherein said nanoparticulate is formed from partially metallic nanoparticles that have plasmon resonance absorption of said electromagnetic radiation.

10. The system of claim 8, wherein said at least partially metallic nanoparticles are elongate.

11. The system of claim 8, wherein said metal is gold or silver.

12. The system of claim 1, wherein each nanoparticulate comprises an aggregate of nanoparticles.

13. The system of claim 12, wherein said aggregate comprises spherical nanoparticles.

14. The system of claim 1, wherein said wavelength spectrum is a range of wavelengths of about 300 nm to about 300 mm.

15. The system of claim 1, wherein said pulse of electromagnetic radiation is optical radiation having a wavelength in the range from 500 nm to 1150 nm.

16. The method of claim 1, wherein said pulse of electromagnetic radiation is about 1 ns to about 100 ns in duration.

17. The system of claim 1, wherein said cancer cells are leukemic cancer cells.

* * * * *